(12) United States Patent
Choi et al.

(10) Patent No.: US 8,227,138 B2
(45) Date of Patent: Jul. 24, 2012

(54) PHOSPHORUS CONTAINING BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

(75) Inventors: Seongwoo Choi, Yongin-si (KR); Jungock Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 887 days.

(21) Appl. No.: 12/263,011

(22) Filed: Oct. 31, 2008

(65) Prior Publication Data
US 2009/0123812 A1   May 14, 2009

(30) Foreign Application Priority Data

Nov. 2, 2007 (KR) .................. 10-2007-0111586
Oct. 9, 2008 (KR) .................. 10-2008-0099352

(51) Int. Cl.
*H01M 8/10* (2006.01)
*C08G 73/06* (2006.01)
*C08J 5/22* (2006.01)

(52) U.S. Cl. .................. 429/491; 429/492; 521/27
(58) Field of Classification Search .................. 521/27; 429/491, 492
See application file for complete search history.

(56) References Cited

U.S. PATENT DOCUMENTS

| | | | |
|---|---|---|---|
| 4,828,699 A | 5/1989 | Soehngen |
| 5,098,985 A | 3/1992 | Harris et al. |
| 5,250,633 A | 10/1993 | Calundann et al. |
| 5,410,012 A | 4/1995 | Connell et al. |
| 5,525,436 A | 6/1996 | Savinell et al. |
| 5,637,670 A | 6/1997 | Connell et al. |
| 5,945,233 A | 8/1999 | Onorato et al. |
| 6,042,968 A | 3/2000 | Onorato et al. |
| 6,482,946 B1 | 11/2002 | Dettloff et al. |
| 6,620,905 B1 | 9/2003 | Musa |
| 6,855,674 B2 | 2/2005 | Gutierrez |
| 7,094,490 B2 | 8/2006 | Cao et al. |
| 7,157,509 B2 | 1/2007 | Li et al. |
| 7,371,480 B2 | 5/2008 | Ono et al. |
| 7,388,035 B2 | 6/2008 | Kim et al. |
| 7,405,021 B2 | 7/2008 | Gascoyne et al. |
| 7,510,678 B2 | 3/2009 | Kim et al. |
| 7,619,044 B2 | 11/2009 | Lee et al. |
| 7,649,025 B2 | 1/2010 | Kitamura et al. |
| 7,709,579 B2 | 5/2010 | Lehmann et al. |
| 2001/0041283 A1 | 11/2001 | Hitomi |
| 2002/0127474 A1 | 9/2002 | Fleischer et al. |
| 2002/0164516 A1 | 11/2002 | Hasegawa et al. |
| 2003/0190516 A1 | 10/2003 | Tanno |
| 2004/0005493 A1 | 1/2004 | Tanno |
| 2004/0028976 A1 | 2/2004 | Cabasso et al. |
| 2004/0206953 A1 | 10/2004 | Morena et al. |
| 2004/0231143 A1 | 11/2004 | Visco et al. |
| 2004/0241522 A1 | 12/2004 | Ono et al. |
| 2004/0261660 A1 | 12/2004 | Li et al. |

(Continued)

FOREIGN PATENT DOCUMENTS

CN     101220153     7/2008

(Continued)

OTHER PUBLICATIONS

Beletskaya et al., "Arylation of 6H-Dibenzo[c,e][1,2 $\lambda^5$] oxaphosphinine 6-Oxide", Russian Journal of Organic Chemistry, vol. 40, No. 12, 2004, pp. 1782-1786.

(Continued)

*Primary Examiner* — Gregg Cantelmo
(74) *Attorney, Agent, or Firm* — Stein McEwen, LLP

(57) ABSTRACT

A phosphorus containing monomer, a polymer thereof, an electrode for a fuel cell including the polymer, an electrolyte membrane for a fuel cell including the polymer, and a fuel cell including the electrode. The phosphorus containing monomer is represented by Formula 1:

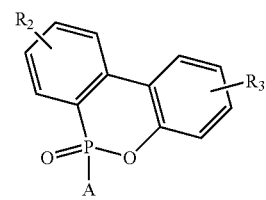

<Formula 1>

Group A is represented by:

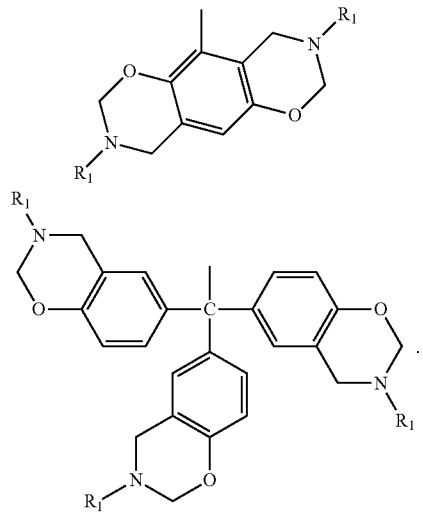

5 Claims, 13 Drawing Sheets

U.S. PATENT DOCUMENTS

| | | |
|---|---|---|
| 2005/0074651 A1 | 4/2005 | Kidai et al. |
| 2005/0084728 A1 | 4/2005 | Kim et al. |
| 2005/0089744 A1 | 4/2005 | Kim et al. |
| 2005/0130006 A1 | 6/2005 | Hoshi et al. |
| 2005/0142413 A1 | 6/2005 | Kimura et al. |
| 2005/0247908 A1 | 11/2005 | Keller et al. |
| 2006/0078774 A1 | 4/2006 | Uensal et al. |
| 2006/0241192 A1 | 10/2006 | Kitamura et al. |
| 2007/0020507 A1 | 1/2007 | Kim et al. |
| 2007/0141426 A1 | 6/2007 | Choi et al. |
| 2007/0184323 A1 | 8/2007 | Lee et al. |
| 2007/0200994 A1 | 8/2007 | Yanagisawa |
| 2007/0238723 A1 | 10/2007 | Goble et al. |
| 2007/0275285 A1 | 11/2007 | Choi et al. |
| 2008/0020264 A1 | 1/2008 | Sun et al. |
| 2008/0045688 A1 | 2/2008 | Lin et al. |
| 2008/0050633 A1 | 2/2008 | Kwon et al. |
| 2008/0118817 A1 | 5/2008 | Lee et al. |
| 2008/0145743 A1 | 6/2008 | Choi et al. |
| 2008/0157422 A1 | 7/2008 | Lee et al. |
| 2009/0075147 A1 | 3/2009 | Kitamura et al. |
| 2009/0117436 A1 | 5/2009 | Choi et al. |
| 2009/0117440 A1 | 5/2009 | Choi et al. |
| 2010/0273087 A1 | 10/2010 | Choi et al. |
| 2011/0189581 A1 | 8/2011 | Choi et al. |

FOREIGN PATENT DOCUMENTS

| | | |
|---|---|---|
| DE | 2034 887 | 1/1972 |
| DE | 603 02 673 | 8/2006 |
| EP | 1 247 844 | 10/2002 |
| EP | 1 253 661 | 10/2002 |
| EP | 1 760 110 | 3/2007 |
| EP | 1 881 549 | 1/2008 |
| JP | 05-283082 | 10/1993 |
| JP | 5-283082 | 10/1993 |
| JP | 10-25343 | 1/1998 |
| JP | 11-503262 | 3/1999 |
| JP | 11-97011 | 4/1999 |
| JP | 2001-19844 | 1/2001 |
| JP | 2001-270891 | 10/2001 |
| JP | 2001-271070 | 10/2001 |
| JP | 2002-260682 | 9/2002 |
| JP | 2003-12747 | 1/2003 |
| JP | 2003-12924 | 1/2003 |
| JP | 2003-286320 | 10/2003 |
| JP | 2003-327694 | 11/2003 |
| JP | 2004-43547 | 2/2004 |
| JP | 2004-103494 | 4/2004 |
| JP | 2004-149779 | 5/2004 |
| JP | 2004-179514 | 6/2004 |
| JP | 2005-41936 | 2/2005 |
| JP | 2005-82690 | 3/2005 |
| JP | 2005-283082 | 10/2005 |
| JP | 2006-339065 | 12/2006 |
| JP | 2007-70631 | 3/2007 |
| JP | 2007-214108 | 8/2007 |
| KR | 10-2006-0011831 | 2/2006 |
| KR | 10-2006-0055291 | 5/2006 |
| KR | 10-2007-0025626 | 3/2007 |
| KR | 10-2007-0025627 | 3/2007 |
| KR | 10-0745741 | 7/2007 |
| KR | 10-2007-0102579 | 10/2007 |
| KR | 2007-102579 | 10/2007 |
| WO | WO 96/13872 | 5/1996 |
| WO | WO 00/51992 | 9/2000 |
| WO | WO 02/14334 | 2/2002 |
| WO | WO 02/057279 | 7/2002 |
| WO | WO 03/072638 | 9/2003 |
| WO | WO 2004/009708 | 1/2004 |
| WO | WO 2004/101509 | 11/2004 |
| WO | WO 2005/000955 | 1/2005 |
| WO | WO 2006/132207 | 12/2006 |

OTHER PUBLICATIONS

Yamada et al., "A Novel Synthesis of 6-Hydroxyalkyl- and 6-Hydroxy-aralkyl-6H-dibenz[c,e][1,2]oxaphosphorin 6-Oxides [1]". vol. 27, 1990, pp. 845-850.

U.S. Office Action dated Jul. 11, 2011, issued in corresponding U.S. Appl. No. 12/208,492.

B. Antalek. "Using Pulsed Gradient Spin Echo NMR for Chemical Mixture Analysis: How to Obtain Optimum Results.", Concepts in Magnetic Resonance (2002) vol. 14(4), pp. 225-258.

S. Viel et al. "Diffusion-Ordered NMR Spectroscopy: A Versatile Tool for the Molecular Weight Determination of Uncharged Polysaccharides.", Biomacromolecules (2003) vol. 4, pp. 1843-1847.

D. A. Jayawickrama et al. "Polymer additives mixture analysis using pulsed-field gradient NMR spectroscopy.", Magn.Reson. Chem (1998), vol. 36, pp. 755-760.

K. Nishinari et al. "Soulution Properties of Pullulan.", Macromolecules (1991) vol. 24, pp. 5590-5593.

L.C. Van Gorkom et al. "Analysis of DOSY and GPC-NMR Experiments on Polymers by Multivariate Curve Resolution.", Journal Of Magnetic Resonance (1998) vol. 130, pp. 125-130.

A. Chen et al. "Determination of Molecular Weight Distributions for Polymers by Diffusion-Ordered NMR.", J. Am. Chem. Soc. (1995) vol. 117, pp. 7965-7970.

Hajime Kimura et al. "Epoxy Resin Cured by Bisphenol a Based Benzoxazine.", Journal of Applied Polymer Science (1998), vol. 68, pp. 1903-1910.

Schuster, Martin F.H., et al., "Anhydrous Proton-Conducting Polymers", Annu. Rev. Mater. Res., vol. 33, 2003, pp. 233-261.

Yamada, M. et al., "Anhydrous proton conducting polymer electrolytes based on poly(vinylphosphonic acid)-heterocyclic composite material", Polymer, vol. 46, No. 9, 2005, pp. 2986-2992.

Pu, H., et al., "Proton Transport in Polybenzimidazole Blended with $H_3PO_4$ or $H_2SO_4$", J. Polymer Science, Part B: Polymer Physics, vol. 40, 2002, pp. 663-669.

Kim, Hyoung-Juhn et al. *Polybenzimidazoles for High Temperature Fuel Cell Application*. Macromol. Rapid Commun. 2004, vol. 25, pp. 1410-1413.

Ueda, Mitsuru et al. *Poly(benzimidazole) Synthesis by Direct Reaction of Methoxyphthalic Acids and Tetramine*. J. Poly. Sci. Part A: Polym. Chem, 27 pp. 2815-2818 (1989).

Choi et al., "Synthesis, characterization and thermal degradation of functional benzoxazine monomers and polymers containing phenylphosphine oxide", Polymer Degradation and Stability, vol. 91, No. 5, May 1, 2006, pp. 1166-1178.

Low, Hong Yee, et al. "Structural Effects of Phenols On the Thermal and Thermo-oxidative Degradation of Polybenzoxazines". Polymer, vol. 40, No. 15. Jul. 1999. pp. 4365-4376.

Kim, H.J., et al. "Synthesis and Thermal Characterization of Polybenzoxazines Based On Acetylene-functional Monomers". Polymer, vol. 40, No. 23. Nov. 1999. pp. 6565-6573.

Shen, Shyan Bob, et al. "Synthesis and Characterization of Polyfunctional Naphthoxazines and Related Polymers". Journal of Applied Polymer Science vol. 61, No. 9. 1996, pp. 1595-1605.

Human translation of JP 2003-286320, A. Takeichi et al., Oct. 2003.
Human translation of JP 2004-103494, Kimura et al., Apr. 2004.
Machine translation of JP 2004-149779, Sakaguchi et al., May 2004.
European Search Report issued in European Patent Application No. 06254551.2-2115 on Nov. 21, 2006.
European Office Action issued in corresponding European Patent Application No. 07250814.6 on Oct. 30, 2007.
European Search Report issued in European Patent Application No. 08104319.2 on Oct. 13, 2008.
European Search Report issued in European Patent Application No. 08157494.9 on Nov. 24, 2008.
European Office Action issued in corresponding EP Application No. 08164095.5 on Dec. 4, 2008.
European Search Report issued in European Patent Application No. 08164096.3 on Jan. 20, 2009.
European Search Report issued in European Patent Application No. 08166328.8 on Jan. 22, 2009.
Extended European Search Report issued in European Patent Application No. 08168032.4 on Feb. 3, 2009.
European Search Report issued in European Patent Application No. 08168404.5 on Feb. 10, 2009.
Extended European Search Report issued in European Patent Application No. 08168404.5 on Apr. 23, 2009.

Japanese Office Action issued in Japanese Patent Application No. 2006-239572 on Feb. 17, 2009.
US Office Action issued in corresponding U.S. Appl. No. 11/947,011 on Jun. 22, 2009.
US Office Action issued in corresponding U.S. Appl. No. 11/947,011 on Jan. 15, 2010.
US Office Action issued in corresponding U.S. Appl. No. 11/947,011 on Mar. 30, 2010.
US Office Action issued in corresponding U.S. Appl. No. 11/514,254 on Jan. 8, 2010.
US Office Action issued in corresponding U.S. Appl. No. 11/514,254 on May 6, 2010.
US Office Action issued in corresponding U.S. Appl. No. 11/765,033 on Sep. 8, 2009.
US Office Action issued in corresponding U.S. Appl. No. 11/765,033 on Jun. 17, 2010.
US Office Action issued in corresponding U.S. Appl. No. 11/743,778 on Sep. 3, 2009.
US Office Action issued in corresponding U.S. Appl. No. 11/743,778 on Feb. 19, 2010.
US Office Action issued in corresponding U.S. Appl. No. 11/765,056 on Jun. 1, 2010.
Japanese Office Action dated Jun. 21, 2011, issued in corresponding Japanese Patent Application No. 2007-309320.
U.S. Office Action dated Aug. 11, 2011, issued in corresponding U.S. Appl. No. 12/247,338.
U.S. Office Action dated Aug. 18, 2011, issued in corresponding U.S. Appl. No. 12/266,039.
U.S. Office Action dated Aug. 31, 2011, issued in corresponding U.S. Appl. No. 12/208,664.
U.S. Office Action dated Sep. 2, 2011, issued in corresponding U.S. Appl. No. 12/262,854.
Tarek AGAG, Journal of Applied Polymer Science, vol. 100, pp. 3769-3777 (2006).
European Search Report dated Jul. 21, 2010 corresponding European Patent Application No. 10164784.0.
European Search Report dated Jul. 21, 2010 issued in corresponding European Patent Application No. 10164785.7.
Seong-Woo Choi et al., "*Synthesis, characterization and thermal degradation of functional benzoxazine monomers and polymers containing phenylphosphine oxide*", Polymer Degradation and Stability 91 (2006), pp. 1166-1178.
Korean Office Action dated Jul. 21, 2010, issued in corresponding Korean Patent Application No. 10-2008-0089999.
Korean Office Action dated Oct. 6, 2010, issued in corresponding Korean Patent Application No. 10-2008-0099549.
212$^{th}$ ECS Meeting—Washington DC, Oct. 7-12, 2007, Program Information, B10—Proton Exchange Membrane Fuel Cells (PEMFC 7) Energy Technology/Physical and Analytical Electrochemistry/Battery/Industrial Electrochemistry and Electrochemical Engineering.
U.S. Appl. No. 11/514,254, filed Sep. 1, 2006, Seongwoo Choi et al., Samsung Electronics Co., Ltd.
U.S. Appl. No. 11/514,831, filed Sep. 5, 2006, Myung-jin Lee et al., Samsung Electronics Co., Ltd.
U.S. Appl. No. 11/743,778, filed May 2, 2007, Seongwoo Choi et al., Samsung Electronics Co., Ltd.
U.S. Appl. No. 11/856,350, filed Sep. 17, 2007, Seongwoo Choi et al., Samsung Electronics Co., Ltd.
U.S. Appl. No. 12/247,338, filed Oct. 8, 2008, Seongwoo-Choi et al., Samsung Electronics Co., Ltd.
U.S. Appl. No. 12/208,664, filed Sep. 11, 2008, Seongwoo Choi et al., Samsung Electronics Co., Ltd.
U.S. Appl. No. 12/262,854, filed Oct. 31, 2008, Seongwoo-Choi et al., Samsung Electronics Co., Ltd.
U.S. Appl. No. 11/947,011, filed Nov. 29, 2007, Seongwoo Choi et al., Samsung Electronics Co., Ltd.
U.S. Appl. No. 12/266,039, filed Nov. 6, 2008, Seongwoo Choi et al., Samsung Electronics Co., Ltd.
U.S. Appl. No. 12/208,492, filed Sep. 11, 2008, Seongwoo Choi et al., Samsung Electronics Co., Ltd.
U.S. Appl. No. 11/765,033, filed Jun. 19, 2007 Hee-young Sun et al., Samsung Electronics Co., Ltd.
U.S. Appl. No. 11/765,056, filed Jun. 19, 2007, Kyung-jung Kwon et al., Samsung Electronics Co., Ltd.
U.S. Office Action dated Jan. 20, 2012, issued in corresponding U.S. Appl. No. 11/947,011.
U.S. Notice of Allowance dated Jan. 31, 2012, issued in corresponding U.S. Appl. No. 12/266,039.
U.S. Office Action dated Feb. 2, 2012, issued in corresponding U.S. Appl. No. 12/208,664.
U.S. Notice of Allowance dated Feb. 3, 2012, issued in corresponding U.S. Appl. No. 12/208,492.
U.S. Notice of Allowance dated Feb. 3, 2012, issued in corresponding U.S. Appl. No. 12/262,854.
STN Registry database entries for RN 35141-82-3, RN 35141-83-4 and RN 35141-84-5, Database entry date Nov. 16, 1984. Accessed Jan. 26, 2012.
Japanese Office Action dated Sep. 20, 2011, issued in corresponding Japanese Patent Application No. 2008-233675.
U.S. Office Action dated Nov. 14, 2011, issued in corresponding U.S. Appl. No. 12/208,492.
U.S. Office Action dated Dec. 22, 2011, issued in corresponding U.S. Appl. No. 12/247,338.
Japanese Office Action dated Oct. 23, 2011, issued in corresponding Japanese Patent Application No. 2007-309320.
Lin et al., "Synthesis and Properties of Flame-Retardant Benzoxazines by Three Approaches", Wiley InterScience, Mar. 12, 2006, pp. 3454-3468.
Hirai et al., "Air-Induced *anti*-Markovnikov Addition of Secondary Phosphine Oxides and H-Phosphinates to Alkenes", National Institute of Advanced Industrial Science and Technology, Organic Letters 2007, vol. 9, No. 1, pp. 53-55.
Beletskaya et al., "Arylation of 6*H*- Dibenzo [c,e][1,2λ5]oxaphosphinine 6-Oxide", Russian Journal of Organic Chemistry, vol. 40, No. 12, 2004, pp. 1782-1786.
Yamada et al., "A Novel Synthesis of 6-Hydroxyalkyl- and 6-Hydroxy-aralkyl-6*H*-dibenz[c,e][1,2]oxaphosphorin 6-Oxides [1]", vol. 27, 1990, pp. 845-850.
Search Report issued in European Patent Application No. 08168081.1 on Jan. 28, 2009.

PHOSPHORUS CONTAINING BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

CROSS-REFERENCE TO RELATED APPLICATIONS

This application claims the benefit of Korean Patent Application No. 2007-111586, filed on Nov. 2, 2007, and Korean Patent Application No. 2008-99352, filed on Oct. 9, 2008 in the Korean Intellectual Property Office, the disclosures of which are incorporated herein by reference.

BACKGROUND OF THE INVENTION

1. Field of the Invention

One or more embodiments of the present invention relate to a phosphorus containing benzoxazine-based monomer, a polymer thereof, an electrode for a fuel cell including the polymer, an electrolyte membrane for a fuel cell including the polymer, and a fuel cell using the electrode

2. Description of the Related Art

Fuel cells that use a polymer electrolyte membrane as an electrolyte operate at a relatively low temperature and can also be small in size, and thus they are expected to be used as an electric power source in electric vehicles or distributed generation systems for homes. As a polymer electrolyte membrane used in polymer electrolyte fuel cells, perfluorocarbon-sulfonic acid-based polymer membranes represented by NAFION® (DuPont Company) are used.

However, such polymer electrolyte membranes need water to retain proton conductivity, and thus the polymer electrolyte membranes need humidifying. In addition, to enhance cell system efficiencies, it is necessary to operate polymer electrolyte membranes at a high temperature of at least 100° C. However, the moisture in polymer electrolyte membranes evaporates at this temperature, and polymer electrolyte membranes can not function as a solid electrolyte.

To address those problems in the art, non-humidified electrolyte membranes which can operate at a high temperature of at least 100° C. under nonhumidified conditions have been developed. For example, U.S. Pat. No. 5,525,436 discloses polybenzimidazole doped with phosphoric acid, and the like as a material constituting non-humidified electrolyte membranes.

In addition, in fuel cells that operate at a low temperature, such as fuel cells using a perfluorocarbonsulfonic acid-based polymer membrane, to prevent gas diffusion in electrodes because of water (formation water) that is produced as electricity is generated in an electrode, particularly a cathode, electrodes using polytetrafluoroethylene (PTFE) as a waterproof agent having hydrophobic properties have been widely used (for example, Japanese Patent Laid-Open Publication No. hei 05-283082).

In addition, phosphoric acid type fuel cells operating at a high temperature of 150 to 200° C. use liquid phosphoric acid as an electrolyte. However, electrodes then may include a large amount of liquid phosphoric acid and that interferes with gas diffusion. Therefore, an electrode catalyst layer that is formed by adding polytetrafluoroethylene (PTFE) as a waterproof agent to an electrode catalyst, and that can prevent fine pores in electrodes from being clogged by phosphoric acid, has been used.

In addition, in fuel cells using a polybenzimidazole (PBI) electrolyte membrane that retains phosphoric acid as a non-humidified electrolyte at a high temperature, in order to reduce contact between the electrodes and the electrolyte membrane, methods of impregnating electrodes with liquid phosphoric acid and of increasing the loading amount of metal catalysts have been tried. However, such fuel cells do not exhibit improved properties, and thus there is a need for further improvement.

In addition, in the case of supplying air to a cathode in a solid polymer electrolyte doped with phosphoric acid, the fuel cell requires an aging time of about 1 week even if the composition of the cathode is optimized. By supplying oxygen to the cathode instead of air, performance of the cathode can be improved and the aging time can also be reduced. However, supplying of oxygen to the cathode is a commercial obstacle to realizing widespread use of the cathode. In addition, a polymer electrolyte membrane formed from PBI does not have satisfactory mechanical properties and chemical stability at a high temperature and does not have the capability of retaining phosphoric acid.

SUMMARY OF THE INVENTION

One or more embodiments of the present invention include a phosphorus containing benzoxazine-based monomer having excellent thermal resistance and resistance to phosphoric acid, a polymer thereof, an electrode for a fuel cell including the polymer, an electrolyte membrane for a fuel cell including the polymer and a fuel cell including the electrode.

To achieve the above and/or other aspects and advantages, one or more embodiments of the present invention may include a phosphorus containing benzoxazine-based monomer represented by Formula 1 below:

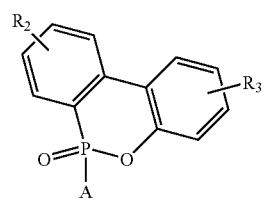

<Formula 1> wherein A is a substituted or unsubstituted $C_1$-$C_{20}$ heterocyclic group, a substituted or unsubstituted $C_4$-$C_{20}$ cycloalkyl group, or a substituted or unsubstituted $C_1$-$C_{20}$ alkyl group, and $R_2$ and $R_3$ are each, independently, hydrogen, a $C_1$-$C_{20}$ alkyl group, a $C_1$-$C_{20}$ alkoxy group, a $C_6$-$C_{20}$ aryl group, a $C_6$-$C_{20}$ aryloxy group, a $C_1$-$C_{20}$ heteroaryl group, a $C_1$-$C_{20}$ heteroaryloxy group, a $C_4$-$C_{20}$ cycloalkyl group, a $C_1$-$C_{20}$ heterocyclic group, a halogen, a cyano group, or a hydroxyl group.

To achieve the above and/or other aspects and advantages, one or more embodiments of the present invention may include a polymer of the phosphorus containing benzoxazine-based monomer described above, wherein the polymer thereof is a polymerization product of the phosphorus containing benzoxazine-based monomer described above or a polymerization product between the phosphorus containing benzoxazine-based monomer described above and a crosslinkable compound.

To achieve the above and/or other aspects and advantages, one or more embodiments of the present invention may include an electrode for a fuel cell, the electrode comprising a catalyst layer containing the polymer of the phosphorus containing benzoxazine-based monomer.

To achieve the above and/or other aspects and advantages, one or more embodiments of the present invention may include a fuel cell comprising a cathode; an anode; and an electrolyte membrane disposed between the cathode and the anode, wherein at least one of the cathode and the anode comprises a catalyst layer containing the polymer of the phosphorus containing benzoxazine-based monomer.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings, of which.

DETAILED DESCRIPTION OF THE EMBODIMENTS

Figure 1:
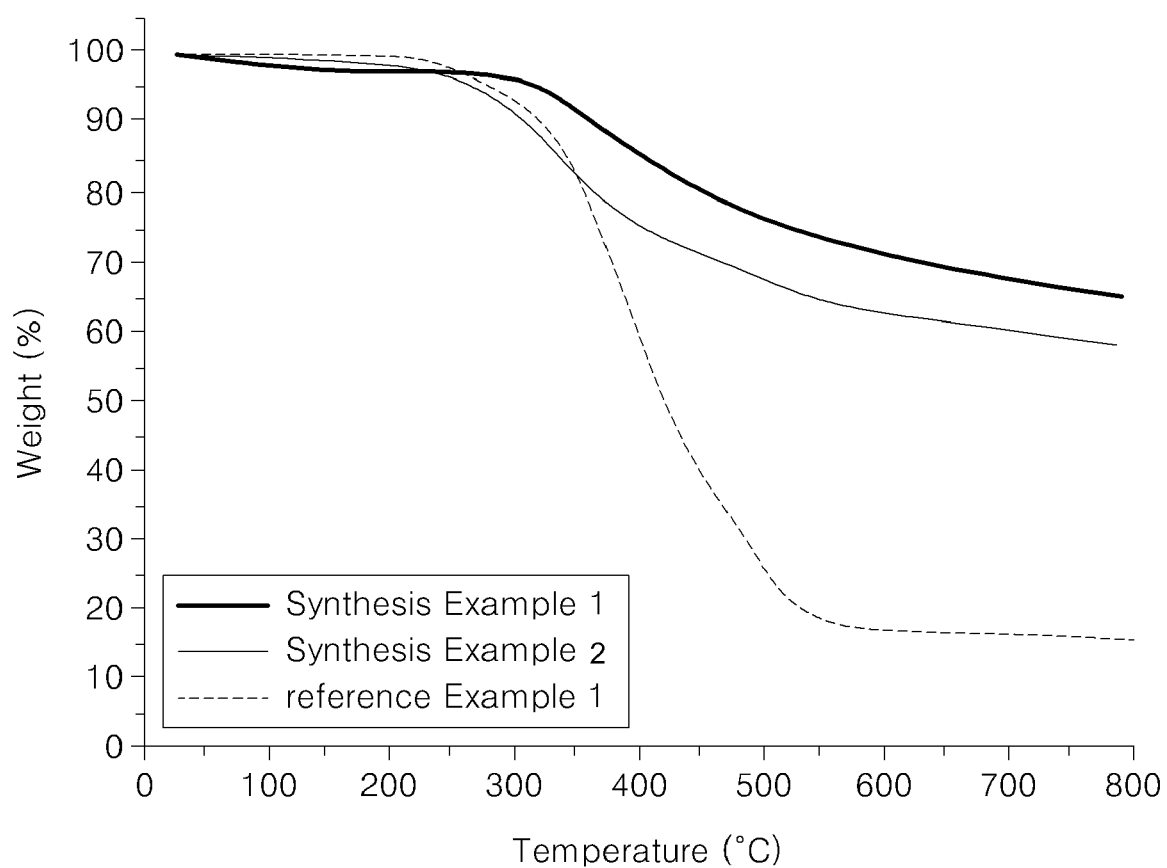
FIG. 1 is a graph showing thermogravimetric analysis (TGA) results of a compound represented by Formula 4 prepared in Synthesis Example 1, a compound represented by Formula 5 prepared in Synthesis Example 2, and t-BuPh-a prepared in Reference Example 1.

Reference will now be made in detail to the present embodiments of the invention, examples of which are illustrated in the accompanying drawings. The embodiments are described below, by referring to the figures, to explain the present invention.

A phosphorus containing benzoxazine-based monomer according to an embodiment of the present invention is represented by Formula 1 below:

<Formula 1>

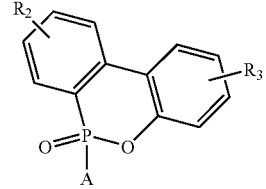

wherein A is a substituted or unsubstituted $C_1$-$C_{20}$ heterocyclic group, a substituted or unsubstituted $C_4$-$C_{20}$ cycloalkyl group, or a substituted or unsubstituted $C_1$-$C_{20}$ alkyl group, and $R_2$ and $R_3$ are each, independently, hydrogen, a $C_1$-$C_{20}$ alkyl group, a $C_1$-$C_{20}$ alkoxy group, a $C_6$-$C_{20}$ aryl group, a $C_6$-$C_{20}$ aryloxy group, a $C_1$-$C_{20}$ heteroaryl group, a $C_1$-$C_{20}$ heteroaryloxy group, a $C_4$-$C_{20}$ cycloalkyl group, a $C_1$-$C_{20}$ heterocyclic group, a halogen, a cyano group, or a hydroxyl group.

In particular, A may be one of the groups represented by the following formulae:

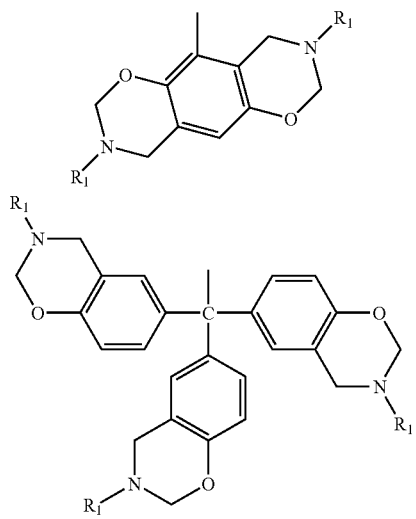

wherein $R_1$ is hydrogen, a $C_1$-$C_{20}$ alkyl group, a $C_1$-$C_{20}$ alkoxy group, a $C_6$-$C_{20}$ aryl group, a $C_6$-$C_{20}$ aryloxy group, a halogenated $C_6$-$C_{20}$ aryl group, a halogenated $C_6$-$C_{20}$ aryloxy group, a $C_1$-$C_{20}$ heteroaryl group, a $C_1$-$C_{20}$ heteroaryloxy group, a halogenated $C_1$-$C_{20}$ heteroaryl group, a halogenated $C_1$-$C_{20}$ heteroaryloxy group, a $C_4$-$C_{20}$ cycloalkyl group, a halogenated $C_4$-$C_{20}$ cycloalkyl group, a $C_1$-$C_{20}$ heterocyclic group, or a halogenated $C_1$-$C_{20}$ heterocyclic group.

The phosphorus containing benzoxazine-based monomer according to another embodiment of the present invention may be at least one monomer selected from compounds represented by Formulae 2 and 3 below:

<Formula 2>

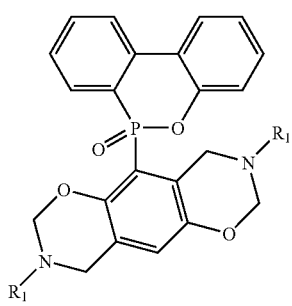

<Formula 3>

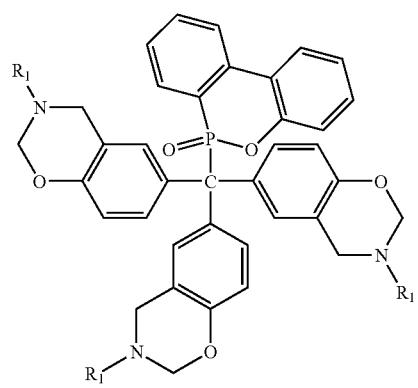

wherein $R_1$ is one group selected from groups represented by the following formulae:

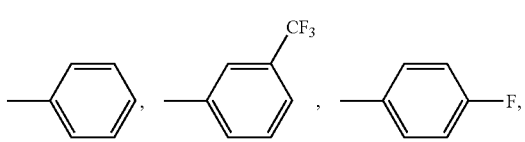

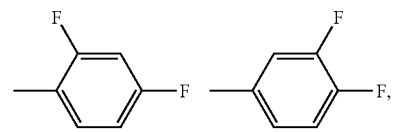

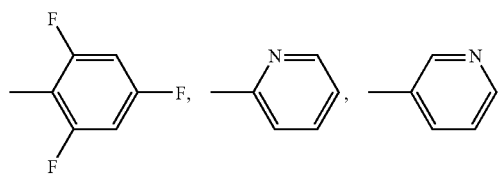

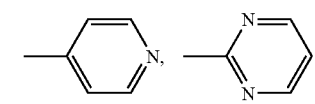

The phosphorus containing benzoxazine-based monomer according to an embodiment of the present invention has excellent thermal stability and capability of retaining phosphoric acid. Thus, when the phosphorus containing benzoxazine-based monomer is used in the formation of an electrode, the amount of phosphoric acid flowing into the electrode increases, resulting in improved wettability of the electrode.

In the case of the phosphorus containing benzoxazine-based monomer of Formulae 2 and 3, where R1 is particularly a fluorine-substituted phenyl group, by introducing a phosphorus-containing functional group into a fluorine-containing benzoxazine-based system, the advantages of a fluorine-containing polymer, such as excellent oxygen transmission, thermal resistance, and resistance to phosphoric acid can be obtained. In addition, the compatibility of all three-phases, that is, gas phase (fuel gas or oxidized gas)-liquid phase (phosphoric acid)-solid phase (catalyst) can be enhanced.

In addition, if the phosphorus containing benzoxazine-based monomer according to an embodiment of the present invention is polymerized with a crosslinkable compound such as PBI by introducing 9,10-dihydro-9-oxa-10-phosphaphenanthrene-10-oxide (DOPO) thereinto, greater covalent bonding can be introduced. Moreover, the phosphorus containing benzoxazine-based monomer includes a —P=O functional group that can maximize both intramolecular hydrogen bonding and intermolecular hydrogen bonding, and thus, when the phosphorus containing benzoxazine-based monomer is co-polymerized with a crosslinkable compound, the crosslinkable sites increase. Thus, by using the phosphorus containing benzoxazine-based monomer, a fuel cell that can have excellent thermal stability and durability at an operating temperature, thereby having a long lifetime, can be prepared.

In addition, when the phosphorus containing benzoxazine-based monomer is simultaneously used for forming an electrode and an electrolyte membrane, the compatibility of the interface between the electrolyte membrane and the electrode is enhanced. Thus, cell performances can be maximized.

Examples of the compound represented by Formula 2 or 3 include compounds represented by Formulae 4 through 10 below.

<Formula 4>

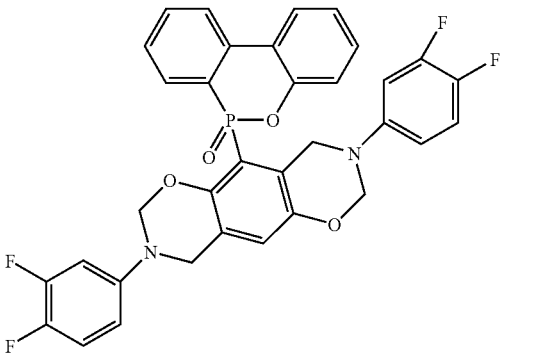

<Formula 5>

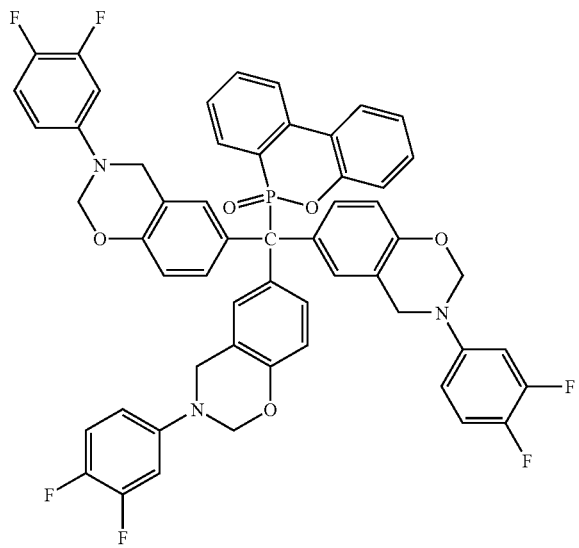

<Formula 6>

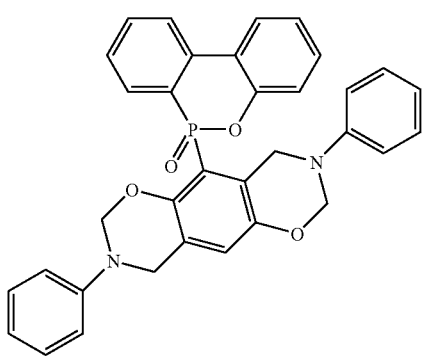

<Formula 7>

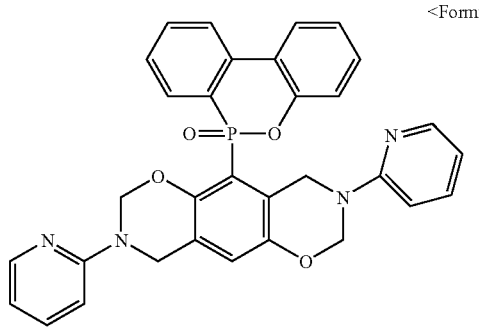

<Formula 8>

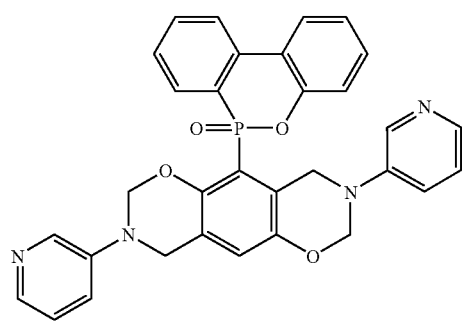

<Formula 9>

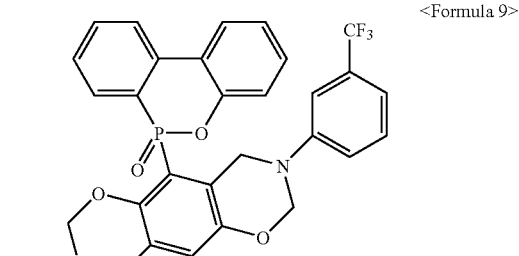

<Formula 10>

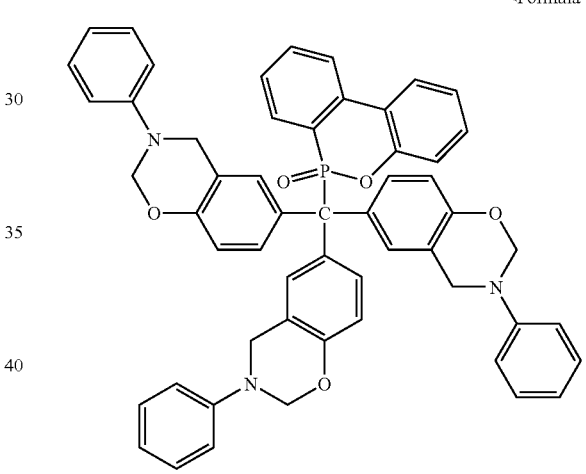

Hereinafter, a method of preparing the phosphorus containing benzoxazine-based monomer of Formula 1 according to an embodiment of the present invention will be described. As an embodiment of the present invention, a method of preparing the compound represented by Formula 2 or 3 will now be described; however, the other compounds described above can be synthesized in a manner similar to the preparation method according to the current embodiment of the present invention.

Referring to Reaction Schemes 1 and 2 below, the compound of Formula 2 can be prepared by heating DOPO-containing diol (A), formaldehyde or para-formaldehyde (B) and an amine compound (C) without a solvent or adding a solvent to A, B and C and then refluxing the mixture, and thereafter working up the resultant. In Reaction Scheme 2, the compound of Formula 3 may be prepared in the same manner as in Reaction Scheme 1, except that DOPO-containing triol (A') is used instead of DOPO-containing diol (A).

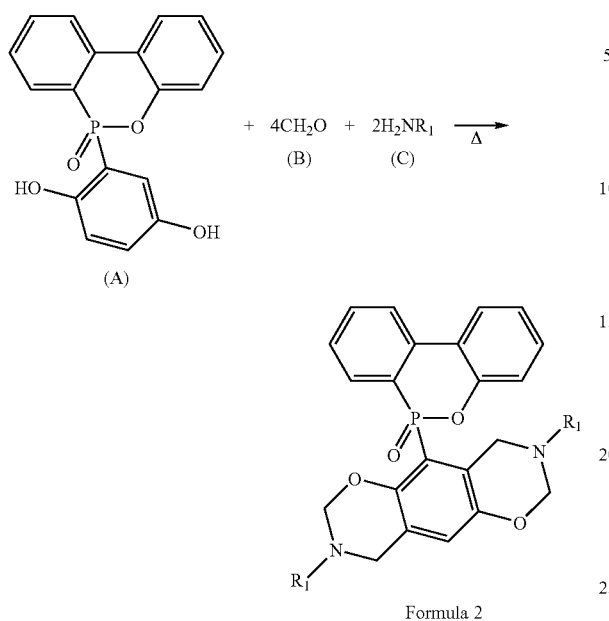

Formula 2

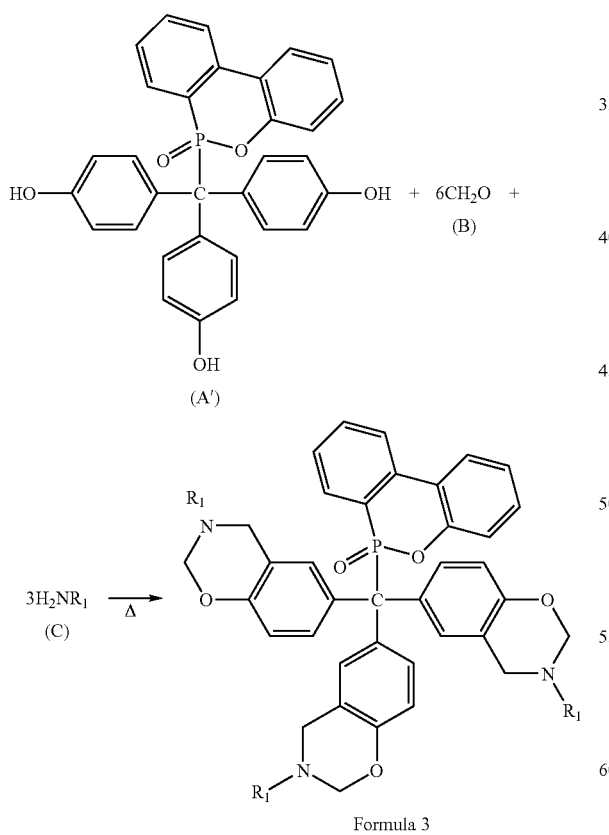

Formula 3

In Reaction Schemes 1 and 2, R1 is selected from the groups represented by the following formulae, that is, the same groups as defined in Formulae 2 or 3, above:

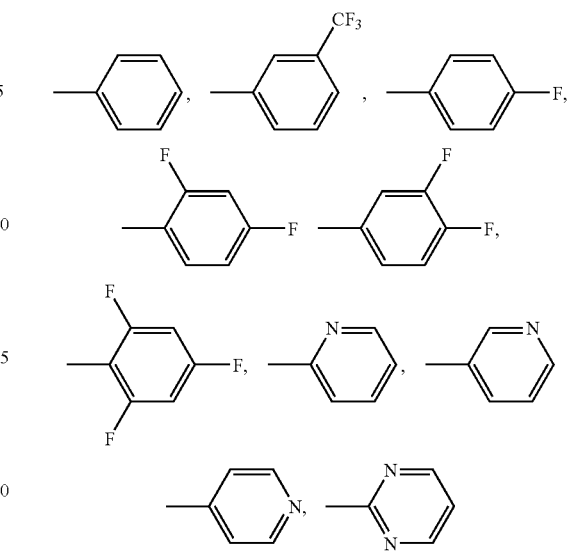

The solvent used in the reaction described above may be 1,4-dioxane, chloroform, dichloromethane, THF, or the like. The heating temperature is adjusted to a temperature at which the solvent can be refluxed, preferably in a range of 80 to 120° C., and in particular to a temperature of about 110° C.

As a non-limiting embodiment of the work-up process, the resultant reaction mixture is washed with an aqueous 1N NaOH solution and water and dried using a drying agent such as magnesium sulfate, and then the resultant is filtered and evaporated under reduced pressure in order to remove the solvent from the resultant, and dried to obtain a target material.

The DOPO-containing diol (A) used in Reaction Scheme 1 can be prepared by reacting DOPO and p-benzoquinone as shown in Reaction Scheme 3 below.

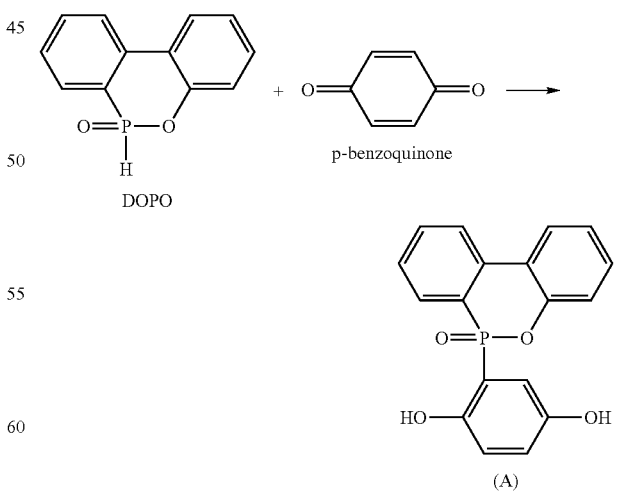

In addition, DOPO-containing triol (A') can be prepared by reacting DOPO and rosolic acid as shown in Reaction Scheme 4 below.

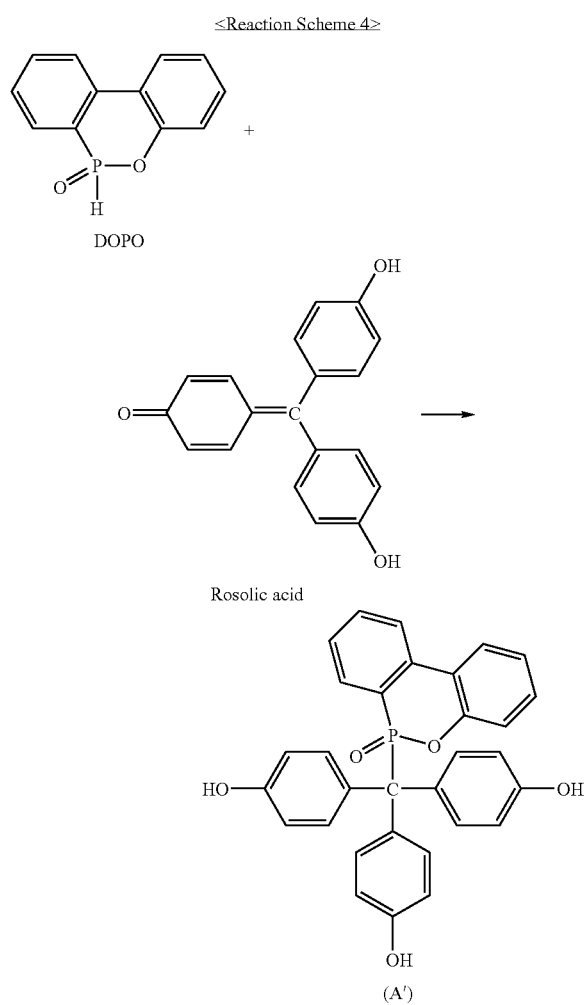

Conditions of the reactions of Reaction Schemes 3 and 4 are not particularly limited. However, in the case of Reaction Scheme 3, DOPO-containing diol (A) can be synthesized by reacting DOPO and p-benzoquinone at 125° C. for 4 hours using 2-ethoxyethanol as a solvent, and in the case of Reaction Scheme 4, the reaction can be performed under solvent reflux. For example, the reaction may be performed at 90° C. for at least 24 hours when ethanol is used as a solvent.

The $C_1$-$C_{20}$ alkyl group used herein may be methyl, ethyl, propyl, isobutyl, sec-butyl, pentyl, iso-amyl, hexyl, or the like. At least one hydrogen atom of the alkyl group may be further substituted with a halogen atom, a $C_1$-$C_{20}$ alkyl group substituted with a halogen atom (for example, $CCF_3$, $CHCF_2$, $CH_2F$, $CCl_3$, and the like), a hydroxyl group, a nitro group, a cyano group, an amino group, an amidino group, hydrazine, a hydrazone, a carboxyl group or a salt thereof, a sulfonic acid group or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_1$-$C_{20}$ heterocyclic group, or a $C_6$-$C_{20}$ heteroarylalkyl group.

The aryl group used herein is used alone or in combination, and refers to a $C_6$-$C_{20}$ carbocyclic aromatic system containing at least one ring, wherein the rings can be attached to each other using a pendant method or fused with each other. The term "aryl" refers to an aromatic radical, including phenyl, naphthyl, tetrahydronaphthyl, or the like. At least one hydrogen atom of the aryl group may be substituted with the same substituents as in the alkyl group described above.

The aryloxy group used herein may be a phenoxy group, a naphthyloxy group, a tetrahydronaphthyloxy group, or the like. At least one hydrogen atom of the aryloxy group may be substituted with the same substituents as in the alkyl group described above.

The heteroaryl group used herein refers to a monovalent, monocyclic or bicyclic aromatic bivalent organic compound that contains 1, 2 or 3 hetero atoms selected from the group consisting of N, O, P, and S and has 1 to 20 carbon atoms. The heteroayl may be pyrazinyl, furanyl, thienyl, pyridyl, pyrimidinyl, isothiazolyl, oxazolyl, thiazolyl, triazolyl, 1,2,4-thiadiazolyl, or the like. At least one hydrogen atom of the heteroaryl group may be substituted with the same substituents as in the alkyl group described above. In addition, the halogenated heteroaryl group used herein refers to a heteroaryl group substituted with a hetero atom such as fluorine, chlorine, and the like.

The heteroaryloxy group used herein may be pyrazinyloxy, furanyloxy, thienyloxy, pyridyloxy, pyrimidinyloxy, isothiazolyloxy, oxazolyloxy, thiazolyloxy, triazolyloxy, 1,2,4-thiadiazolyloxy, or the like. At least one hydrogen atom of the heteroaryloxy group may be substituted with the same substituents as in the alkyl group described above. The halogenated heteroaryloxy group used herein refers to a heteroaryloxy group substituted with a hetero atom such as fluorine, chlorine, and the like.

The heterocyclic group used herein refers to a $C_1$-$C_{20}$ group with a 5-10 membered ring containing a hetero atom such as nitrogen, sulfur, phosphorus, oxygen, and the like. At least one hydrogen atom of the heterocyclic group may be substituted with the same substituents as in the alkyl groups described above. In addition, the halogenated heterocyclic group used herein refers to a heterocyclic group substituted with a hetero atom such as fluorine, chlorine, and the like.

The cycloalkyl group used herein may be a cyclohexyl group, a cyclopentyl group, or the like. At least one hydrogen atom of the cycloalkyl group may be substituted with the same substituent as in the alkyl group described above. In addition, the halogenated cycloalkyl group used herein refers to a cycloalkyl group substituted with a hetero atom such as fluorine, chlorine, and the like.

An embodiment of the present invention also provides a polymer of the phosphorus containing benzoxazine-based monomer of Formula 1. The polymer can be prepared by dissolving the phosphorus containing benzoxazine-based monomer of Formula 1 in a solvent, and then polymerizing the resultant by heat treatment. Herein, the heat treatment temperature is in the range of 180 to 250° C. When the heat treatment temperature is less than 180° C., the reactivity (speed) of the polymerization is lower; on the other hand, when the heat treatment temperature is greater than 250° C., unreacted compound is produced, thereby reducing the yield of the product.

In this reaction, a polymerization catalyst or the like can be used, if necessary. The solvent used in this reaction may be N-methylpyrolidone (NMP), dimethylacetamide (DMAc), or the like, and the amount of the solvent may be in the range of 5 to 30 parts by weight based on 100 parts by weight of the phosphorus containing benzoxazine-based monomer of Formula 1.

An embodiment of the present invention also provides a polymer of the benzoxazine-based monomer that is a polymerization product between the phosphorus containing benzoxazine-based monomer of Formula 1 and a crosslinkable compound. The crosslinkable compound may be at least one of polybenzimidazole, a polybenzimidazole-base complex, polybenzothiazole, polybenzoxazole and polyimide. The amount of the crosslinkable compound may be in the range of 5 to 95 parts by weight based on 100 parts by weight of the phosphorus containing benzoxazine-based monomer of Formula 1.

When the polymer of the phosphorus containing benzoxazine-based monomer is used in the formation of an electrode for a fuel cell, oxygen permeability can be improved although air is used in the cathode, and wettability of phosphoric acid ($H_3PO_4$) to the electrode and thermal stability can also be improved. In addition, when the polymer of the phosphorus containing benzoxazine-based monomer is used in the formation of an electrolyte membrane for a fuel cell, the thermal stability and durability of the electrolyte membrane at operating temperatures are improved. A fuel cell using the electrode and the electrolyte membrane described above can also operate at a high temperature with no humidity, and have enhanced thermal stability and excellent power generation efficiency.

An electrode for a fuel cell according to an embodiment of the present invention includes a catalyst layer comprising a polymer that is a polymerization product of the phosphorus containing benzoxazine-based monomer represented by Formula 1 or a polymerization product of the phosphorus containing benzoxazine-based monomer represented by Formula 1 and a crosslinkable compound. The catalyst layer includes a catalyst.

The polymer of the phosphorus containing benzoxazine-based monomer represented by Formula 1 is used as a binder of the electrode, and in particular, can act as the only binder. Thus, a separate binder such as those commonly used is not necessary for the electrode.

The polymer of the phosphorus containing benzoxazine-based monomer of Formula 1 is a material that improves the wettability of phosphoric acid, and the amount of the polymer may be in the range of 0.1 to 65 parts by weight based on 100 parts by weight of the catalyst. When the amount of the polymer of the phosphorus containing benzoxazine-based monomer of Formula 1 is less than 0.1 parts by weight based on 100 parts by weight of the catalyst, the wettability of phosphoric acid in an electrode is insufficiently improved. On the other hand, when the amount of the polymer of the phosphorus containing benzoxazine-based monomer of Formula 1 is greater than 65 parts by weight based on 100 parts by weight of the catalyst, membrane forming properties may be decreased.

The catalyst may be platinum alone, or an alloy or mixture of platinum and at least one metal selected from the group consisting of gold, palladium, rhodium, iridium, ruthenium, tin, molybdenum, cobalt, and chrome. Alternatively, the catalyst may be a support catalyst in which the catalyst metal is loaded on a carbonaceous support. In particular, the catalyst may be a catalyst metal including at least one of Pt, PtCo, and PtRu, or a support catalyst in which the catalyst metal is loaded on a carbonaceous support.

Although a binder is not necessary, the electrode may further include a binder such as those conventionally used in the preparation of an electrode for a fuel cell. The binder may be at least one selected from the group consisting of poly(vinylidenefluoride), polytetrafluoroethylene (i.e., perfluoroethylene or PTFE), tetrafluoroethylene-hexafluoroethylene copolymer (i.e., fluorinated ethylene propylene or FEP), styrene butadiene rubber (SBR) and polyurethane. The amount of the binder may be in the range of 0.1 to 50 parts by weight based on 100 parts by weight of the catalyst. When the amount of the binder is less than 0.1 parts by weight based on 100 parts by weight of the catalyst, the adhesion between electrodes is so poor that it is difficult to maintain the shape of the catalyst layer. On the other hand, when the amount of the binder is greater than 50 parts by weight based on 100 parts by weight of the catalyst, electric resistance in the electrode is increased. The type and amount of the crosslinkable compound are the same as described above.

A method of preparing the electrode for a fuel cell described above is as follows. First, a catalyst is dispersed in a solvent. The solvent used is N-methylpyrolidone (NMP), dimethylacetamide (DMAc), or the like, and the amount of the solvent is in the range of 100 to 1,000 parts by weight based on 100 parts by weight of the catalyst. A mixture of the phosphorus containing benzoxazine-based monomer of Formula 1 and the solvent is added to the dispersion and mixed together, and then the resultant is stirred. The mixture may further include a binder. The solvent is, again, N-methylpyrolidone (NMP), dimethylacetamide (DMAc), or the like.

The resultant is coated on the surface of a carbon support to prepare an electrode. Herein, the carbon support may be fixed on a glass substrate in order to easily coat the resultant thereon. The coating method is not particularly limited, but may be coating using a doctor blade, bar coating, screen printing, or the like. The coated resultant is dried at a temperature in the range of 20 to 150° C., to remove the solvent. The drying time is dependent on the drying temperature, and is in the range of 10 to 60 minutes.

As can be seen from the description of the method of preparing an electrode above, the electrode for a fuel cell, which is finally obtained, does not contain the phosphorus containing benzoxazine-based monomer of Formula 1, but contains a polymer thereof. The phosphorus containing benzoxazine-based monomer of Formula 1 is polymerized during the drying process described above and/or while a fuel cell including the electrode operates.

If a crosslinking agent is further added to the mixture of the phosphorus containing benzoxazine-based monomer, the solvent, and the binder, the prepared electrode includes a polymer of the benzoxazine-based monomer and a crosslinkable compound. The method of preparing a fuel cell including the electrode for a fuel cell including a polymer of the benzoxazine-based monomer and a crosslinkable compound is the same as that just described.

Hereinafter, an electrolyte membrane and a method of preparing the electrolyte membrane according to an embodiment of the present invention will be described. An electrolyte membrane formed using a crosslinkable compound is described herein. However, when an electrolyte membrane is prepared only using the phosphorus containing benzoxazine-based monomer of Formula 1, the preparation process is the same as those described herein, except that the crosslinkable compound was not used.

As a first method, the phosphorus containing benzoxazine-based monomer represented by Formula 1 is blended with a crosslinkable compound, and the mixture is cured at a temperature in the range of 50 to 250° C., and preferably 80 to 220° C. The cured mixture is impregnated with a proton conductor such as an acid to prepare an electrolyte membrane.

The crosslinkable compound may be at least one compound selected from the group consisting of polybenzimidazole (PBI), a polybenzimidazole-base complex, polybenzothiazole, polybenzoxazole, and polyimide. The polybenzimidazole-base complex is disclosed in Korean Patent Application No. 2007-102579. The amount of the crosslinkable compound may be in the range of 5 to 95 parts by weight based on 100 parts by weight of the phosphorus containing benzoxazine-based monomer of Formula 1.

When the amount of the crosslinkable compound is less than 5 parts by weight, the proton conductivity may be decreased since phosphoric acid may not impregnate the membrane. On the other hand, when the amount of the crosslinkable compound is greater than 95 parts by weight, gas may permeate the membrane since the crosslinked portion may be soluble in polyphosphoric acid in the presence of an excess amount of phosphoric acid. As a second method, an electrolyte membrane is formed using a mixture of the phosphorus containing benzoxazine-based monomer represented by Formula 1 and a crosslinkable compound without the proton conductor.

The formation of the electrolyte membrane may be performed by a tape casting method, or a conventional coating method. The conventional coating method may be a method in which the mixture is cast on a support using a doctor blade. Herein, a doctor blade with a 250 to 500 μm gap is used.

When a casting method using a doctor blade is used, the process of forming the electrolyte membrane further includes separating the electrolyte membrane from the support, between the time when curing of the mixture occurs and the time when impregnation of the resultant with acid occurs. When it is time to perform the process of separating the electrolyte membrane from the support, the mixture is immersed in distilled water having a temperature in the range of 60 to 80° C.

The support can be any support that can support an electrolyte membrane, for example, a glass substrate, a polyimide film, and the like. When the tape casting method is used, a tape cast membrane is separated from a support such as polyethylene terephthalate before being cured, and then put into an oven. In addition, when a membrane is formed by the tape casting method using a mixture of a benzoxazine-based monomer and polybenzimidazole, a process of filtering the mixture may be further performed.

The tape cast membrane is cured by heat treatment, and then is impregnated with a proton conductor such as acid to form an electrolyte membrane. The proton conductor may be phosphoric acid, a $C_1$-$C_{20}$ organic phosphonic acid, or the like, but is not limited thereto. The $C_1$-$C_{20}$ organic phosphonic acid may be ethyl phosphonic acid, methyl phosphonic acid, etc.

The amount of the proton conductor is in the range of 300 to 1,000 parts by weight based on 100 parts by weight of the total weight of the electrolyte membrane. The concentration of the acid used is not particularly limited. However, in the case of phosphoric acid, 85 wt % of an aqueous phosphoric acid solution is used, and the impregnation time of the phosphoric acid is in the range of 2.5 to 14 hours at 80° C.

A method of preparing a fuel cell using the electrode for a fuel cell according to an embodiment of the present invention will now be described. Any electrolyte membrane that is commonly used in the preparation of fuel cells can be used herein. Alternatively, an electrolyte membrane including a polymer (crosslinked product) of polybenzoxazine-based compounds that is prepared by polymerization of the phosphorus containing benzoxazine-based monomer represented by Formula 1 and a crosslinkable compound can also be used. In particular, performance of the fuel cell may be maximized by using an electrolyte membrane including the polymer of a polybenzoxazine-based compound. For example, the electrolyte membrane that is commonly used in a fuel cell may be a polybenzimidazole electrolyte membrane, a polybenzoxazine-polybenzimidazole copolymer electrolyte membrane, a PTFE porous membrane, or the like.

A method of preparing a membrane-electrode assembly for a fuel cell, according to an embodiment of the present invention, is as follows. The term "membrane and electrode assembly (MEA)" used herein refers to a structure in which an electrode, comprising a catalyst layer and a fuel diffusion layer, is deposited on both surfaces of the electrolyte membrane.

The MEA may be formed by positioning the electrode including the catalyst layer for an electrode described above at both sides of the electrolyte membrane, joining them all together at a high temperature and a high pressure, and then joining a fuel diffusion layer to the catalyst layers. Herein, the joining is performed under a pressure in the range of 0.1 to 3 ton/cm$^2$, and particularly about 1 ton/cm$^2$, in a state reached when the MEA is heated up to a temperature that softens the electrolyte membrane.

Next, a bipolar plate is disposed on each side of the membrane-electrode assembly to prepare a fuel cell. The bipolar plate has grooves used for supplying fuel, and functions as a current collector.

The use of the fuel cell of the present invention is not particularly limited. However, the fuel cell may be preferably used as a polymer electrolyte membrane (PEM) fuel cell.

Hereinafter, the present invention will be described more specifically with reference to the following examples. The following examples are only for illustrative purposes and are not intended to limit the scope of the invention.

SYNTHESIS EXAMPLE 1

Preparation of Compound Represented by Formula 4

3.24 g of DOPO diol (10 mmol), 1.32 g of formaldehyde or para-formaldehyde (44 mmol of formaldehyde), and 2.84 g of 3,4-difluoroaniline (22 mmol) were sequentially added to a 100 ml one-neck round bottomed flask, and then mixed in an oil bath at 90° C. The reaction mixture was transparent in an early stage of the reaction, and about 30 minutes after the reaction, the reaction mixture was converted to a dark brown material in the form of a transparent gel. Herein, the reaction mixture was quenched with tetrahydrofuran (THF) to be cooled to room temperature. The crude product cooled to room temperature was base washed twice by solvent extraction using an aqueous 1N NaOH solution, and then washed once again with deionized water.

After the washing process was completed, the organic layer obtained was dried using MgSO4, and then continuously filtered. The filtrate was removed using a rotary evaporator, and then the purified product was dried in a vacuum oven at 40° C. for 6 hours.

Figure 4:
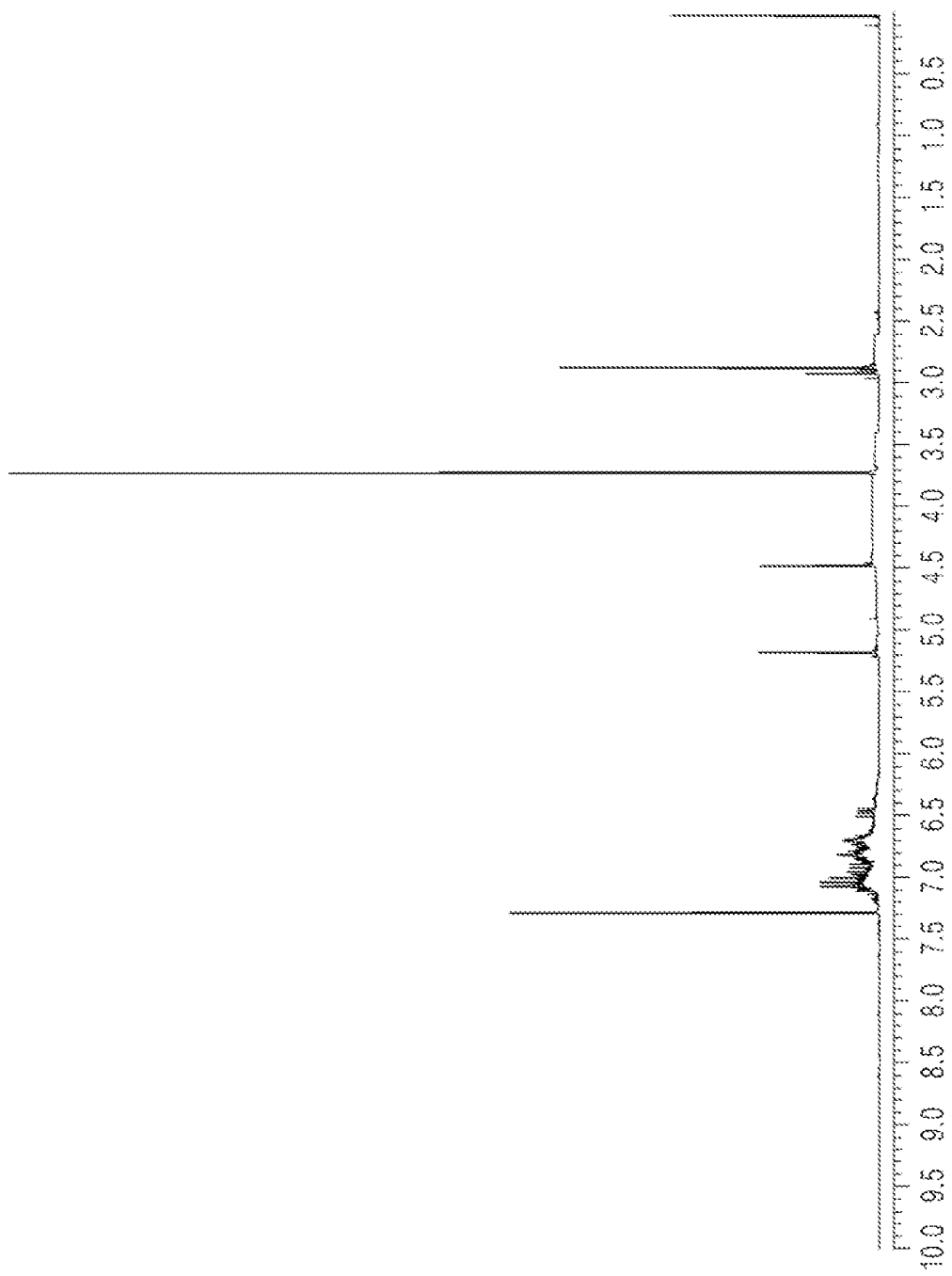
FIG. 4 is a graph showing the nuclear magnetic resonance (NMR) spectrum of DOPO-di-34DFA represented by Formula 4, as prepared in Synthesis Example 1.

The structure of the compound of Formula 4 prepared in Synthesis Example 1 was confirmed by NMR spectrum. FIG. 4 is the NMR spectrum of the structure of the compound of Formula 4 prepared in Synthesis Example 1.

SYNTHESIS EXAMPLE 2

Preparation of Compound Represented by Formula 5

A compound represented by Formula 5 was prepared in the same manner as in Synthesis Example 1, except that 5.07 g of DOPO triol (10 mmol), 1.98 g of formaldehyde or para-formaldehyde (66 mmol of formaldehyde), and 4.26 g of 3,4-difluoroaniline (33 mmol) were added to a 100 ml one-neck round bottomed flask, and mixed together in an oil bath. The structure of the compound of Formula 5 prepared in Synthesis Example 2 was confirmed by NMR spectrum. FIG.

5 is the NMR spectrum of the structure of the compound of Formula 5 prepared in Synthesis Example 2.

SYNTHESIS EXAMPLE 3

Preparation of Compound Represented by Formula 6

Figure 6:
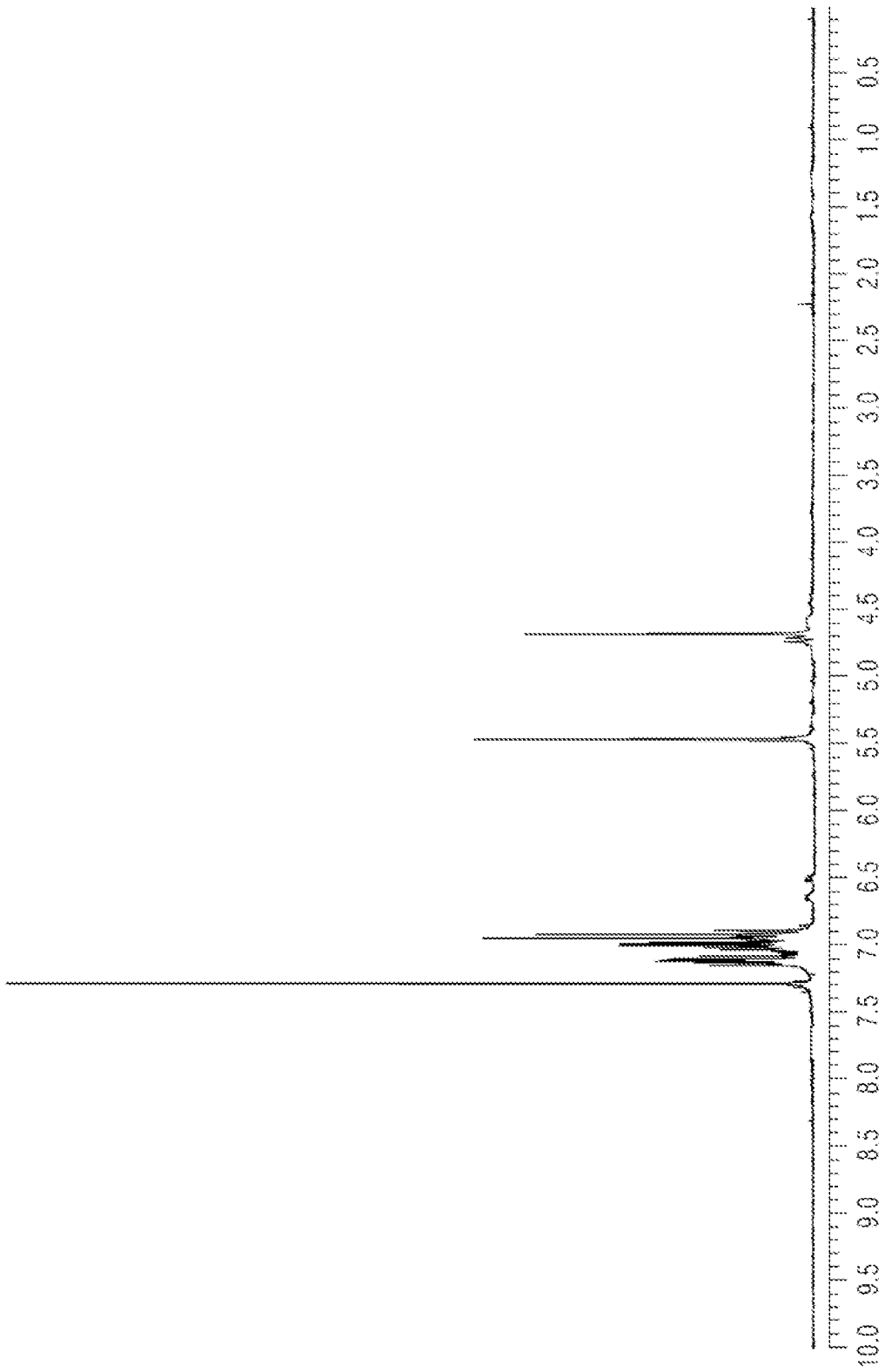
FIG. 6 is a graph showing the nuclear magnetic resonance (NMR) spectrum of DOPO-di-a represented by Formula 6, as prepared in Synthesis Example 3.

A compound represented by Formula 6 was prepared in the same manner as in Synthesis Example 1, except that 2.05 g of aniline (22 mmol) was used instead of 2.84 g of 3,4-difluoroaniline (22 mmol). The structure of the compound of Formula 6 prepared in Synthesis Example 3 was confirmed by NMR spectrum. FIG. 6 is the NMR spectrum of the structure of the compound of Formula 6 prepared in Synthesis Example 3.

SYNTHESIS EXAMPLE 4

Preparation of Compound Represented by Formula 7

A compound represented by Formula 7 was prepared in the same manner as in Synthesis Example 1, except that 6.48 g of DOPO diol (20 mmol), 2.64 g of formaldehyde or paraformaldehyde (88 mmol of formaldehyde), and 4.14 g of 2-aminopyridine (44 mmol) were added to a 100 ml one-neck round bottomed flask.

SYNTHESIS EXAMPLE 5

Preparation of Compound Represented by Formula 8

A compound represented by Formula 8 was prepared in the same manner as in Synthesis Example 1, except that 6.48 g of DOPO diol (20 mmol), 2.64 g of formaldehyde or paraformaldehyde (88 mmol of formaldehyde), and 4.14 g of 3-aminopyridine (44 mmol) were added to a 100 ml one-neck round bottomed flask.

SYNTHESIS EXAMPLE 6

Preparation of Compound Represented by Formula 9

A compound represented by Formula 9 was prepared in the same manner as in Synthesis Example 1, except that 6.48 g of DOPO diol (20 mmol), 2.64 g of formaldehyde or paraformaldehyde (88 mmol of formaldehyde), and 44 mmol of 3-trifluoromethylaniline were added to a 100 ml one-neck round bottomed flask.

SYNTHESIS EXAMPLE 7

Preparation of Compound Represented by Formula 10

A compound represented by Formula 10 was prepared in the same manner as in Synthesis Example 1, except that 5.07 g of DOPO triol (10 mmol), 1.98 g of formaldehyde or paraformaldehyde (66 mmol of formaldehyde), and 33 mmol of aniline were added to a 100 ml one-neck round bottomed flask.

REFERENCE EXAMPLE 1

Preparation of t-BuPh-a 15 g of t-butylphenol (0.1 mol), 6.31 g of formaldehyde or para-formaldehyde (0.21 mol of formaldehyde), and 10.24 g of aniline (0.11 mol) were sequentially added to a 100 ml one-neck round bottomed flask, and then mixed in an oil bath at 90° C.

The reaction mixture was opaque in an early stage of the reaction, and about 30 minutes after the reaction, the reaction mixture was converted to a dark brown material in the form of a transparent gel. The reaction mixture was quenched with tetrahydrofuran (THF) to be cooled to room temperature.

The crude product cooled to room temperature was base washed twice by solvent extraction using an aqueous 1N NaOH solution, and then washed once again with deionized water. After the washing process was terminated, an organic layer obtained was dried using MgSO4, and then continuously filtered. The filtrate was removed using a rotary evaporator, and then the purified product was dried in a vacuum oven at 40° C. for 6 hours to obtain t-BuPh-a. The structure of t-BuPh-a was confirmed by an NMR spectrum as the following formula:

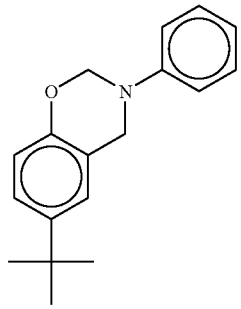

Thermal stabilities of the compound of Formula 4 of Synthesis Example 1, the compound of Formula 5 of Synthesis Example 2, and t-BuPh-a of Reference Example 1 were evaluated using thermogravimetric analysis (TGA). The results are shown in FIG. 1. In FIG. 1, thermogravimetric loss was measured to 800° C.

Referring to FIG. 1, it was confirmed that the compound of Formula 4 and the compound of Formula 5 had smaller thermogravimetric losses at a temperature of 800° C. (or beyond) than that of t-BuPh-a. From the result, it can be seen that the compound of Formula 4 and the compound of Formula 5 have excellent thermal stability compared to t-BuPh-a.

Figure 5:
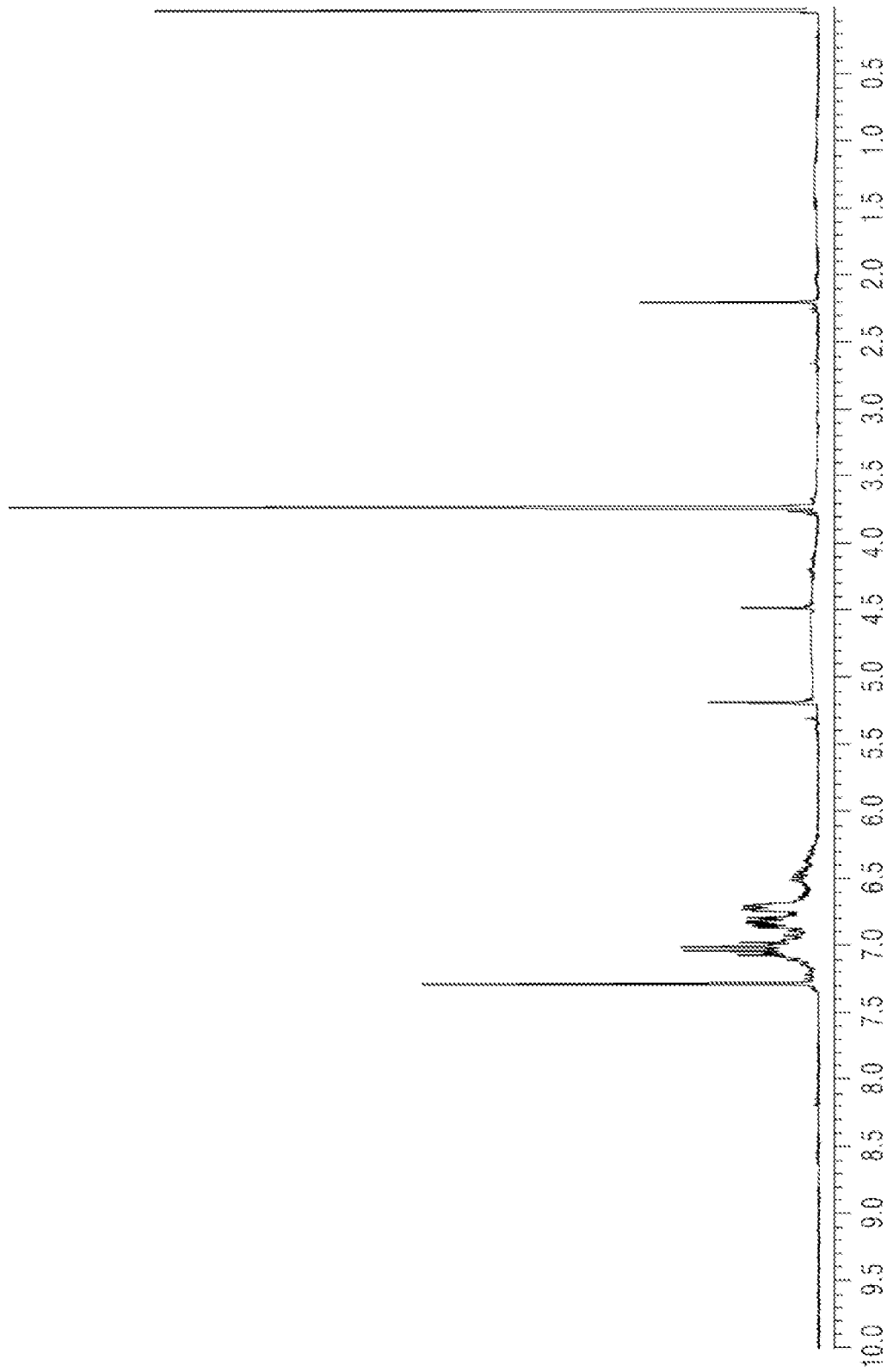
FIG. 5 is a graph showing the nuclear magnetic resonance (NMR) spectrum of DOPO-tri-34DFA represented by Formula 5, as prepared in Synthesis Example 2.

FIGS. 4, 5 and 6 show respectively the NMR spectra of DOPO-di-34DFA represented by Formula 4, DOPO-tri-34DFA represented by Formula 5, and DOPO-di-a represented by Formula 6, prepared in Synthesis Examples 1, 2 and 3. That is, the structure of these compounds is confirmed by the NMR spectra using a Bruker 300 MHz NMR spectrophotometer.

SYNTHESIS EXAMPLE 8

Preparation of Polymer of DOPO-di-34DFA of Formula 4 and PBI 65 parts by weight of DOPO-di-34DFA of Formula 4 and 35 parts by weight of polybenzimidazole (PBI) were blended together, and then the mixture was cured at a temperature in the range of about 180 to 240° C. to obtain a polymer of DOPO-di-34DFA of Formula 4 and PBI.

SYNTHESIS EXAMPLE 9

Preparation of Polymer of DOPO-tri-34DFA of Formula 5 and PBI 65 parts by weight of DOPO-tri-34DFA of Formula 5 and 35 parts by weight of polybenzimidazole (PBI) were blended together, and then the mixture was cured at a temperature in the range of about 180 to 240° C. to obtain a polymer of DOPO-tri-34DFA of Formula 5 and PBI.

Figure 7:
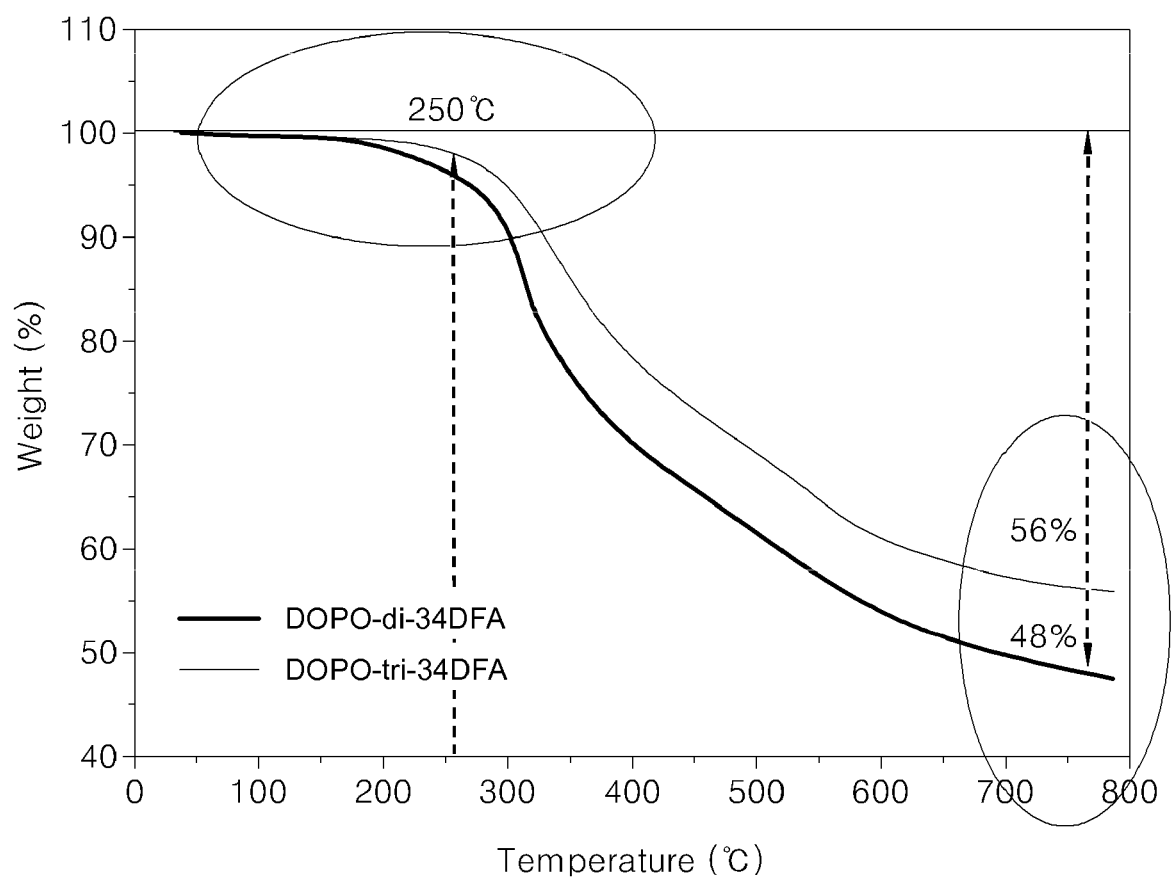
FIG. 7 is a graph showing evaluation results of thermal stabilities using TGA of DOPO-di-34DFA, DOPO-tri-34DFA, and the polymer of DOPO-di-34DFA and PBI that was prepared in Synthesis Example 8.
Figure 8:
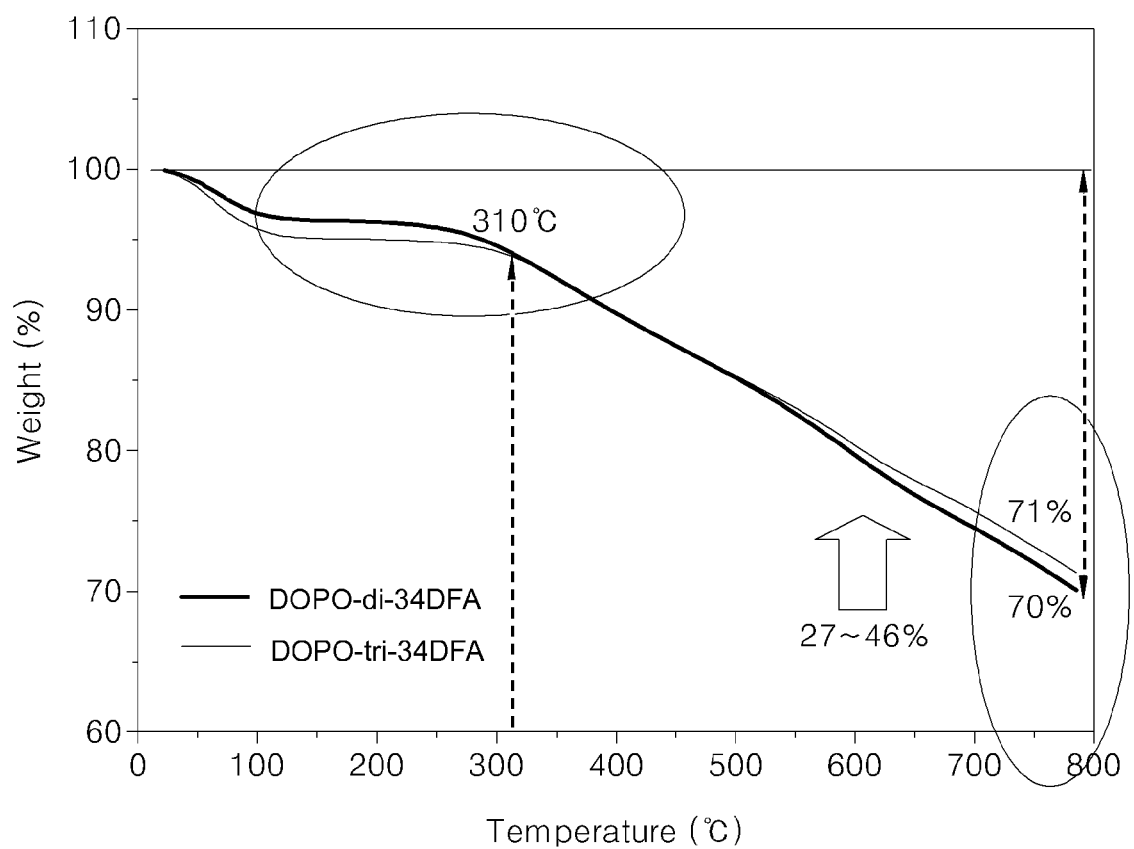
FIG. 8 is a graph showing evaluation results of thermal stabilities using TGA of DOPO-di-34DFA, DOPO-tri-34DFA, and the polymer of DOPO-tri-34DFA and PBI that was prepared in Synthesis Example 9.

Thermal stabilities of DOPO-di-34DFA, DOPO-tri-34DFA, and the polymer of DOPO-di-34DFA and PBI and the polymer of DOPO-tri-34DFA and PBI that were prepared in Synthesis Examples 8 and 9, were evaluated using thermogravimetric analysis (TGA). The results are respectively shown in FIGS. 7 and 8. In FIGS. 7 and 8, thermogravimetric loss was measured to 800° C.

Referring to FIGS. 7 and 8, it can be seen that although DOPO-di-34DFA and DOPO-tri-34DFA have excellent thermal stability, the polymer of DOPO-di-34DFA and PBI and the polymer of DOPO-tri-34DFA and PBI have better thermal stability.

SYNTHESIS EXAMPLE 10

Preparation of Polymer of Compound Represented by Formula 10 and Polybenzimidazole 20 g of the compound represented by Formula 10 and 10.8 g of polybenzimidazole were cured at a temperature of about 220° C. to obtain a polymer of the compound of Formula 10 and polybenzimidazole.

Figure 12:
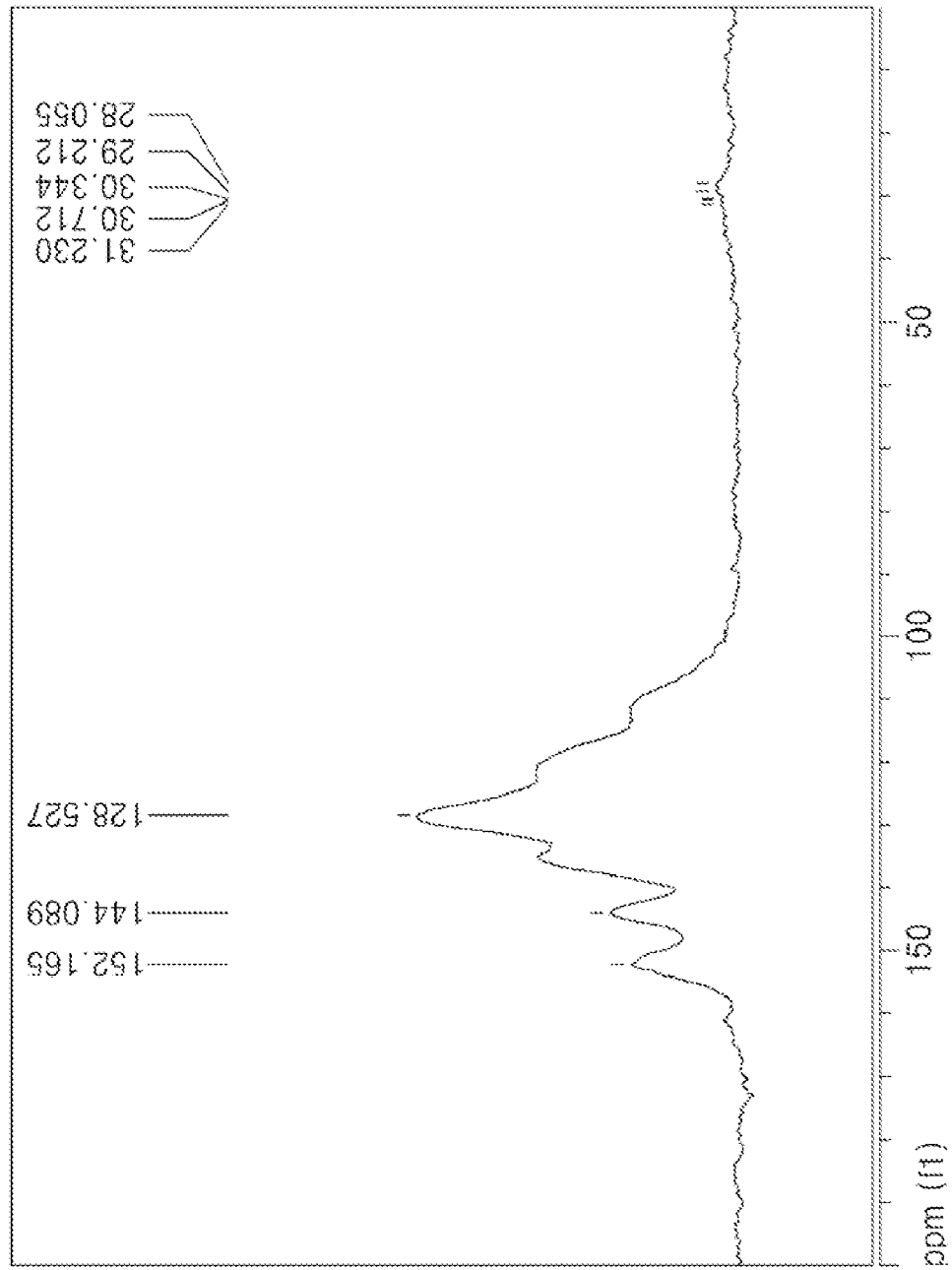
FIG. 12 is a graph showing a solid NMR spectrum of a polymer of the compound represented by Formula 10 and prepared in Synthesis Example 10.

The structure of the solid-phase polymer of the compound of Formula 10 and polybenzimidazole was identified by a solid nuclear magnetic resonance (NMR) spectrum, and the results are shown in FIG. 12. The NMR was performed using a Varian Unity INOVA600 at 600 MHz.

EXAMPLE 1

Preparation of Electrode for Fuel Cell and Fuel Cell Including the Electrode An electrode prepared by the following process was used as a cathode. 1 g of a catalyst in which 50 wt % of PtCo was supported on carbon and 3 g of NMP were added to a stirrer, and the mixture was stirred using a mortar to prepare a slurry. An NMP solution of the compound of Formula 4 of Synthesis Example 1 was added to the slurry to make the resultant contain 0.025 g of the compound of Formula 4. The resultant was stirred further.

Subsequently, an NMP solution of 5 wt % of polyvinylidenefluoride was added to the resultant to make the resultant contain 0.025 g of polyvinylidenefluoride. The resultant was mixed for 10 minutes to prepare the slurry used for forming a cathode catalyst layer.

Carbon paper was cut to a size of 4×7 $cm^2$, fixed on a glass plate, and coated by a doctor blade (Sheen instrument). Herein, the gap interval was adjusted to 600 μm.

The slurry used for forming the cathode catalyst layer was coated on the carbon paper, and the resultant was dried at room temperature for 1 hour, dried at 80° C. for 1 hour, dried at 120° C. for 30 minutes, and dried at 150° C. for 15 minutes to prepare a cathode (a fuel electrode). The loading amount of PtCo in the prepared cathode was 3.0 mg/$cm^2$.

An electrode prepared by the following process was used as an anode. 2 g of a catalyst in which 50 wt % of Pt was supported on carbon and 9 g of NMP were added to a stirrer, and the mixture was stirred for 2 minutes using a high speed stirrer.

Subsequently, a solution in which 0.05 g of polyvinylidenefluoride was dissolved in 1 g of NMP was added to the mixture, and the resultant was further stirred for 2 minutes to prepare the slurry used for forming an anode catalyst layer. The slurry used for forming the anode catalyst layer was coated on carbon paper coated with a microporous layer using a bar coater. As a result, preparation of the anode was completed. The loading amount of Pt in the prepared anode was 1.4 mg/$cm^2$.

Separately, 60 parts by weight of the benzoxazine-based monomer of Formula 11, 3 parts by weight of the benzoxazine-based monomer of Formula 12, and 37 parts by weight of polybenzimidazole were blended together, and then the mixture was cured at about 220° C.

<Formula 11>

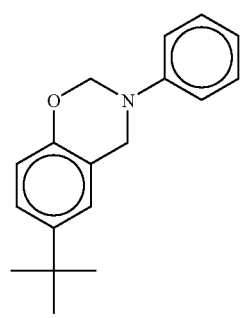

<Formula 12>

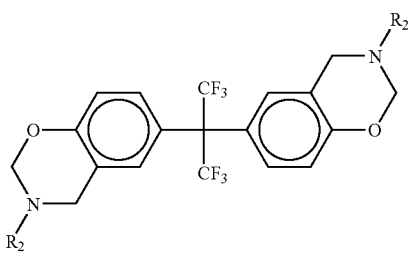

($R_2$ = phenyl group)

Subsequently, the resultant was impregnated with 85 wt % of phosphoric acid at 80° C. for over 4 hours to form an electrolyte membrane. Herein, the amount of phosphoric acid was about 480 parts by weight based on 100 parts by weight of the total weight of the electrolyte membrane.

The loading amount of PtCo in the prepared cathode was about 2.33 mg/$cm^2$, and the loading amount of Pt in the prepared anode was 1.4 mg/$cm^2$. The electrolyte membrane was disposed between the cathode and the anode to prepare a MEA. Herein, the cathode and anode were not impregnated with phosphoric acid.

To prevent gas permeation between the cathode and the anode, a PTFE membrane for a main gasket with a thickness of 200 μm and a PTFE membrane for a subgasket with a thickness of 20 μm were joined and disposed between the electrode and the electrolyte membrane. The pressure applied to the MEA was adjusted to 1, 2, then 3 N-m Torque, step by step, using a wrench to assemble a cell.

Electricity was generated by causing hydrogen to flow into the anode (flowrate: 100 ccm) and causing air to flow into the cathode (flowrate: 250 ccm) at 150° C. under a condition where the electrolyte membrane was not humidified, and properties of the fuel cell thus prepared were measured. Herein, an electrolyte doped with phosphoric acid was used, and the performance of the fuel cell improved as time elapsed. The fuel cell was aged until the operating voltage reached a peak, and then the properties of the fuel cell were finally evaluated. In addition, the area of the cathode and anode was fixed to a size of 2.8×2.8 (7.84 cm²), and the thickness of the cathode was about 430 μm and the thickness of the anode was about 390 μm.

EXAMPLE 2

Preparation of Electrode for Fuel Cell and Fuel Cell Including the Electrode

A cathode was prepared in the same manner as in Example 1, except that the compound of Formula 5 was used instead of the compound of Formula 4, and a fuel cell using the cathode was prepared.

EXAMPLES 3-5

Preparation of Electrode for Fuel Cell and Fuel Cell Including the Electrode

Cathodes were prepared in the same manner as in Example 1, except that the compound of Formula 6 (Example 3), the compound of Formula 7 (Example 4), and the compound of Formula 8 (Example 5) were used instead of the compound of Formula 4, and fuel cells using the cathodes were prepared.

COMPARATIVE EXAMPLE 1

Preparation of Electrode for Fuel Cell and Fuel Cell Including the Electrode

Figure 2:
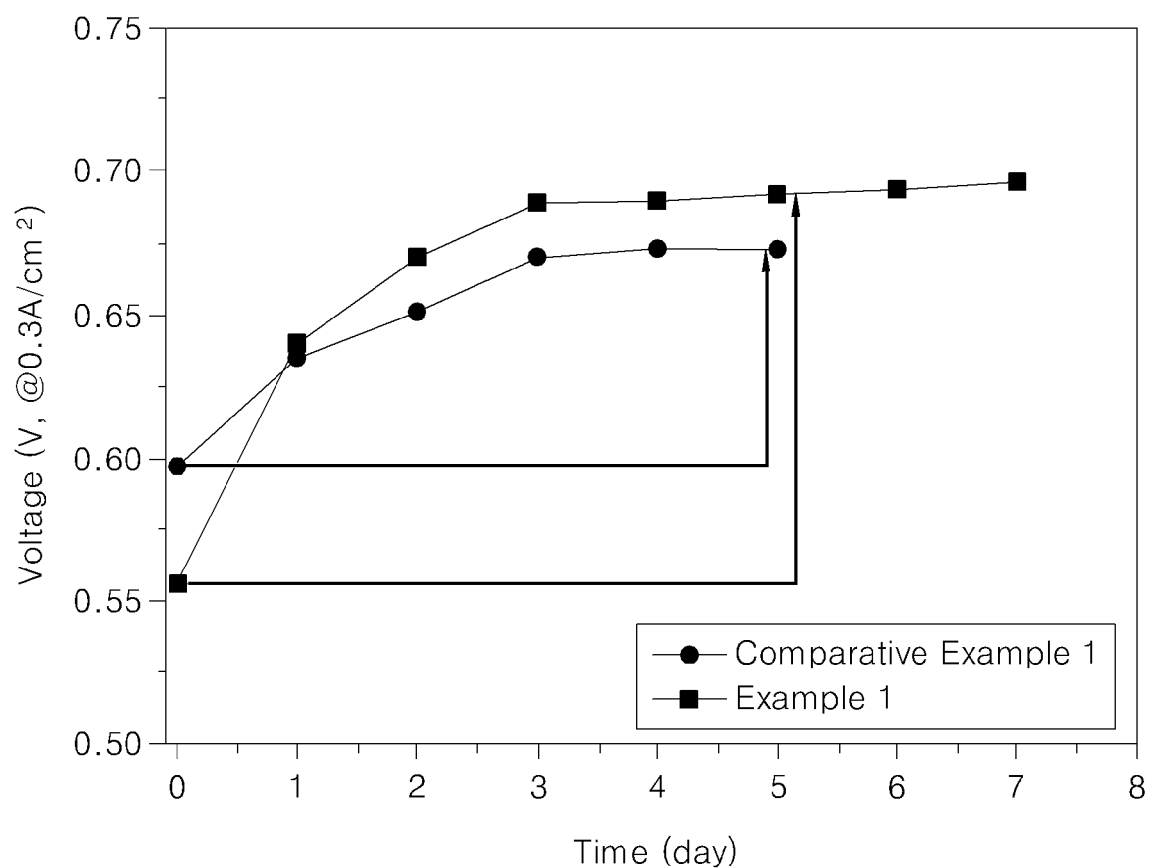
FIG. 2 is a graph showing the changes in voltage as a function of time of fuel cells prepared in Example 1 and Comparative Example 1.

Referring to FIG. 2, although the fuel cell of Example 1 had lower initial performance, it had improved voltage performance through fast activation compared to the fuel cell of Comparative Example 1.

Figure 3:
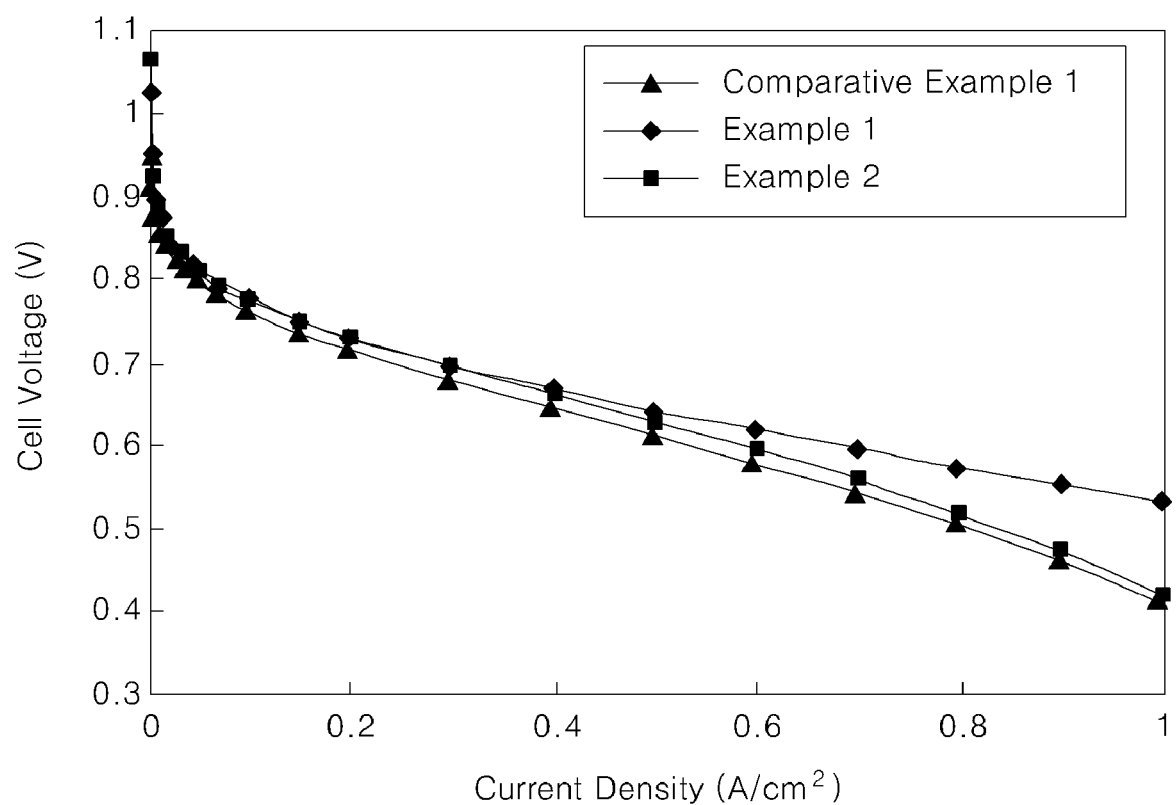
FIG. 3 is a graph showing the change in cell potential as a function of current density of fuel cells prepared in Examples 1 and 2 and Comparative Example 1.

FIG. 3 is a graph showing the measured changes in cell potential as a function of current density of the fuel cells prepared in Examples 1 and 2 and Comparative Example 1.

The fuel cells of Examples 1 and 2 had higher cell potentials compared to the fuel cell of Comparative Example 1.

Cell performances of the fuel cells of Examples 1 through 5 and Comparative Example 1 were measured, and the results are shown in Table 1 below.

TABLE 1

|  | Voltage at 0.3 A/cm² (V) | Mass transfer overpotential η at 0.3 A/cm² (mV) | Kinetic overpotential η at 0.3 A/cm² (mV) | Exchange current density (A/cm²) | Tafel slope (mv/dec) |
|---|---|---|---|---|---|
| Compound of Formula 4 (Example 1) | 0.696 | 15 | 261 | $5.2 \times 10^{-5}$ | 98 |
| Compound of Formula 5 (Example 2) | 0.694 | 18 | 264 | $4.5 \times 10^{-5}$ | 97 |
| Compound of Formula 6 (Example 3) | 0.692 | 14 | 270 | $5.4 \times 10^{-5}$ | 101 |
| Compound of Formula 7 (Example 4) | 0.691 | 19 | 265 | $4.7 \times 10^{-5}$ | 98 |
| Compound of Formula 8 (Example 5) | 0.688 | 18 | 268 | $5.2 \times 10^{-5}$ | 100 |
| Comparative Example 1 | 0.678 | 22 | 277 | $3.8 \times 10^{-5}$ | 97 |

Referring to Table 1, the fuel cells of Examples 1 through 5 had lower mass transfer overpotentials and kinetic overpotentials (versus a standard electrode) and higher exchange current densities compared to the fuel cell of Comparative Example 1. From the results, it was confirmed that the fuel cells of Examples 1 through 5 had higher oxygen transmissions in the catalyst layer. In general, therefore, these embodiments show the higher oxygen transmission, the lower mass transfer overpotential and kinetic overpotential and the higher exchange current density.

EXAMPLE 6

Preparation of an Electrolyte Membrane for a Fuel Cell and a Fuel Cell Using the Electrolyte Membrane An electrode prepared according to the process as follows was used as a cathode. 1 g of a catalyst in which 50% by weight of PtCo is loaded on carbon and 3 g of NMP as a solvent were added to a stirrer, and the mixture was agitated to prepare a slurry. Then, a solution of 5% by weight of polyvinylidenefluoride and NMP was added to the mixture to set the amount of the polyvinylidenefluoride to 0.025 g, and the mixture was mixed for 10 minutes to prepare a slurry for the cathode catalyst layer.

Carbon paper was cut into pieces of 4×7 cm² in size, and the pieces were fixed on a glass plate and coated using a doctor blade (Sheen instrument), wherein the gap interval of the doctor blade was 600 μm. The slurry for the cathode catalyst layer was coated on the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 2.32 mg/cm2.

An electrode prepared according to the process as follows was used as an anode. 2 g of a catalyst in which 50% by weight of Pt is supported on carbon and 9 g of NMP solvent were added to a stirrer and the mixture was agitated in a high-speed agitator for 2 minutes.

Then, a solution of 0.05 g of polyvinylidenefluoride dissolved in 1 g of NMP was added thereto and the mixture was agitated for 2 minutes to prepare a slurry for the anode catalyst layer. The slurry was coated using a bar coater on carbon paper on which a microporous layer had been coated. The amount of loaded Pt in the prepared anode was 1.44 mg/cm2.

Separately, 65 parts by weight of DOPO-tri-34DFA of Formula 5 prepared in Synthesis Example 2 was blended with 35 parts by weight of polybenzimidazole (PBI), and the mixture was cured at about 220° C. Then, the resultant was impregnated with 85% by weight of phosphoric acid at 80° C. for longer than 4 hours to prepare an electrolyte membrane. In this example, the amount of phosphoric acid was about 530 parts by weight based on 100 parts by weight of electrolyte membrane.

A membrane electrode assembly (MEA) was prepared by interposing the electrolyte membrane between the cathode and the anode. In this example, the cathode and anode were not impregnated with phosphoric acid.

A 200 μm PTFE membrane for a main gasket and a 20 μm PTFE membrane for a sub gasket were overlapped on an interface between the electrodes and electrolyte membrane in order to prevent gas permeation between the cathode and the anode. The pressure applied to the MEA was adjusted to 1, 2, then 3 N-m Torque, step by step, using a wrench to assemble a cell.

Characteristics of fuel cells were measured while operating by supplying hydrogen to the anode at 100 ccm and supplying air to the cathode at 250 ccm, while the electrolyte membrane was not hydrated, at 150° C. Since cell efficiency increases with time by using the electrolyte doped with phosphoric acid, the final efficiency was measured after the fuel cell was aged until the operational voltage was maximized. The area of the cathode and the anode was fixed to 2.8×2.8=7.84 cm$^2$, and the thickness of the cathode was about 430 μm and the thickness of the anode was about 390 μm although the thicknesses of the cathode and the anode may vary according to the distribution of thickness of the carbon paper.

EXAMPLE 7

Preparation of an Electrolyte Membrane for a Fuel Cell and a Fuel Cell Using the Electrolyte Membrane An electrolyte membrane and a fuel cell using the electrolyte membrane were prepared in the same manner as in Example 6, except that DOPO-di-34DFA of Formula 4 prepared in Synthesis Example 1 was used instead of DOPO-tri-34DFA of Formula 5 prepared in Synthesis Example 2.

Figure 9:
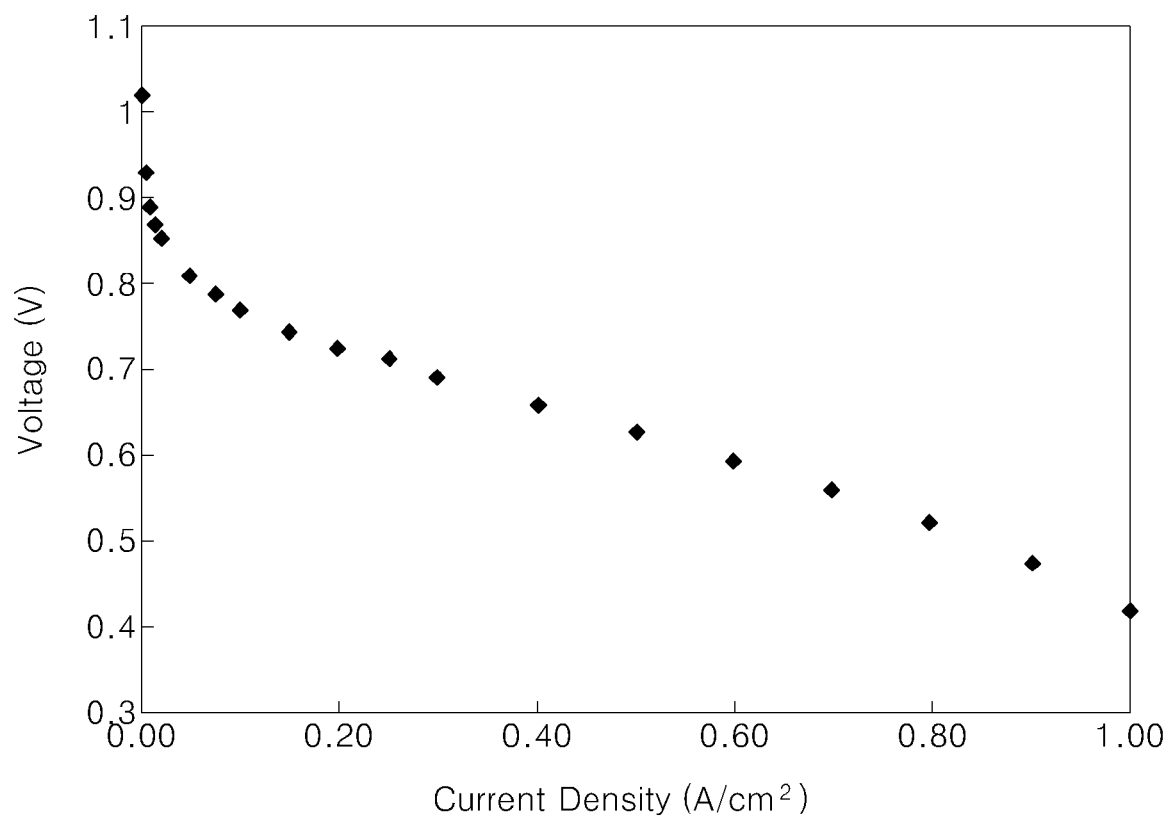
FIG. 9 is a graph showing the voltage change as a function of current density of the fuel cell prepared in Example 6.

The voltage change as a function of current density of the fuel cell prepared in Example 6 was measured, and the results are shown in FIG. 9. Referring to FIG. 9, it can be seen that the fuel cell of Example 6 has excellent cell voltage.

Figure 10:
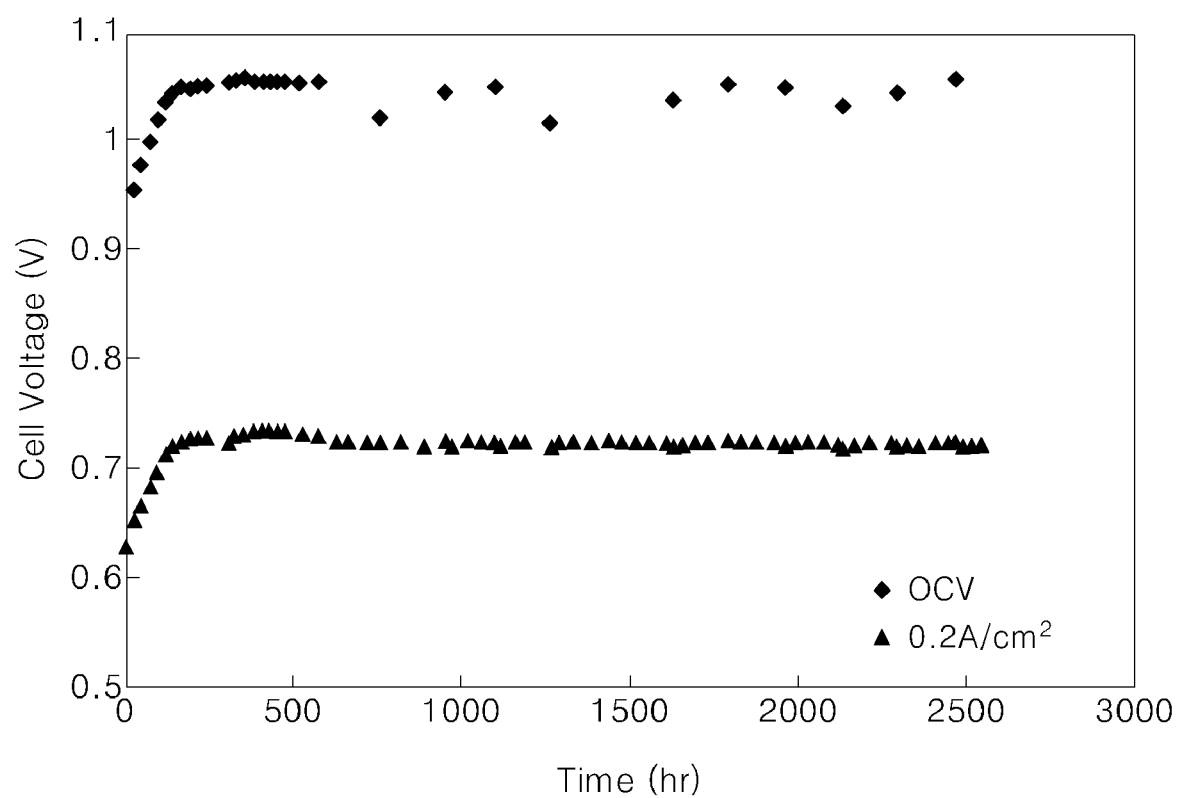
FIG. 10 is a graph showing the change in cell voltage as a function of time of the fuel cell prepared in Example 6.

In addition, the change in cell voltage as a function of time of the fuel cell of Example 6 was measured, and the results are shown in FIG. 10. In FIG. 10, "OCV" denotes an open circuit voltage, and "0.2 A/cm2" denotes cell voltage at a current density of 0.2 A/cm2. Referring to FIG. 10, the fuel cell of Example 6 shows nearly no voltage drop to 2500 hours.

Figure 11:
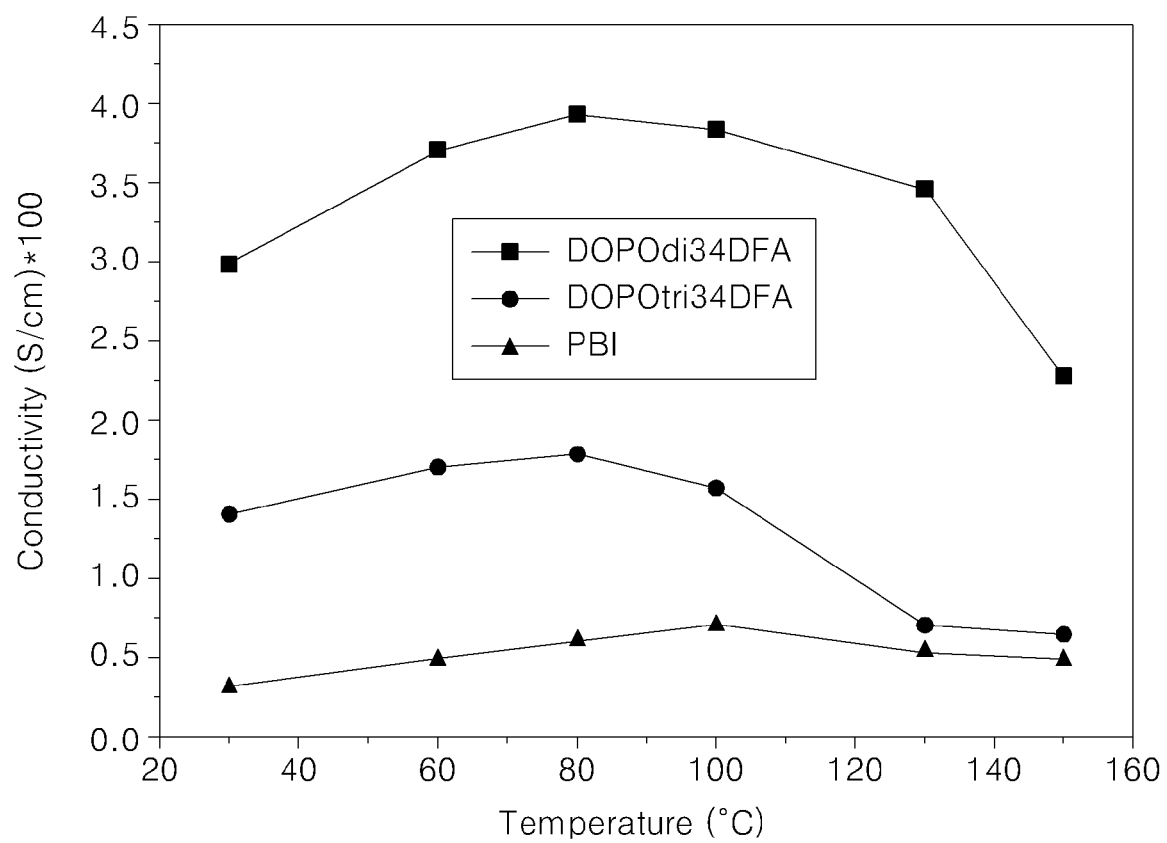
FIG. 11 is a graph showing the changes in conductivity as a function of temperature of the electrolyte membranes prepared in Examples 6 and 7.

The changes in conductivity as a function of temperature of the electrolyte membranes prepared in Examples 6 and 7 were measured, and the results are shown in FIG. 11. In FIG. 11, the results of an electrolyte membrane formed of PBI as a reference sample are also shown. Referring to FIG. 11, the electrolyte membranes of Examples 6 and 7 have higher conductivity compared with the electrolyte membrane formed of PBI.

EXAMPLE 8

Preparation of Fuel Cell

An electrode prepared according to the process as follows was used as a cathode. 1 g of a catalyst in which 50% by weight of PtCo is loaded on carbon and 3 g of NMP as a solvent were added to a stirrer, and the mixture was agitated to prepare a slurry. A solution of DOPO-di-34DFA of Formula 4 prepared in Synthesis Example 1 and NMP was added to the slurry to set the amount of DOPO-di-34DFA of Formula 4 to 0.025 g, and the mixture was further agitated.

Then, a solution of 5% by weight of polyvinylidenefluoride and NMP was added to the mixture to set the amount of the polyvinylidenefluoride to 0.025 g, and the mixture was stirred for an additional 10 minutes to prepare a slurry for a cathode catalyst layer. Carbon paper was cut into pieces of 4×7 cm$^2$ in size, and the pieces were fixed on a glass plate and coated using a doctor blade (Sheen instrument), wherein the gap interval of the doctor blade was 600 μm.

The slurry for the cathode catalyst layer was coated on the carbon paper and dried at room temperature for 1 hour, at 80° C. for 1 hour, at 120° C. for 30 minutes and at 150° C. for 15 minutes to prepare the cathode (a fuel electrode). The amount of loaded Pt/Co in the prepared cathode was 2.32 mg/cm$^2$.

An electrode prepared according to the process as follows was used as an anode. 2 g of a catalyst in which 50% by weight of Pt is supported on carbon and 9 g of NMP solvent were added to a stirrer and the mixture was agitated in a high-speed agitator for 2 minutes.

Then, a solution of 0.05 g of polyvinylidenefluoride dissolved in 1 g of NMP was added thereto and agitated for 2 minutes to prepare a slurry for the anode catalyst layer. The slurry was coated using a bar coater on carbon paper on which a microporous layer had been coated. The amount of loaded Pt in the prepared anode was 1.44 mg/cm2.

Separately, 65 parts by weight of DOPO-tri-34DFA of Formula 5 prepared in Synthesis Example 2 was blended with 35 parts by weight of polybenzimidazole (PBI), and the mixture was cured at about 220° C. Then, the resultant was impregnated with 85% by weight of phosphoric acid at 80° C. for longer than 4 hours to prepare an electrolyte membrane. In this example, the amount of phosphoric acid was about 530 parts by weight based on 100 parts by weight of electrolyte membrane.

A membrane electrode assembly (MEA) was prepared by interposing the electrolyte membrane between the cathode and the anode. In this example, the cathode and anode were not impregnated with phosphoric acid.

A 200 μm PTFE membrane for a main gasket and a 20 μm PTFE membrane for a sub gasket were overlapped on an interface between the electrodes and electrolyte membrane in order to prevent gas permeation between the cathode and the anode. The pressure applied to the MEA was adjusted to 1, 2, then 3 N-m Torque, step by step, using a wrench to assemble a cell.

Characteristics of fuel cells were measured while operating by supplying hydrogen to the anode at 100 ccm and supplying air to the cathode at 250 ccm, while the electrolyte membrane was not hydrated, at 150° C. Since cell efficiency increases with time by using the electrolyte doped with phosphoric acid, the final efficiency was measured after the fuel cell was aged until operational voltage was maximized. The area of the cathode and the anode was fixed to 2.8×2.8=7.84 cm², and the thickness of the cathode was about 430 μm and the thickness of the anode was about 390 μm although the thicknesses of the cathode and the anode may vary according to the distribution of thickness of the carbon paper.

COMPARATIVE EXAMPLE 2

Preparation of Fuel Cell

A fuel cell was prepared in the same manner as in Example 8, except that a polybenzimidazole (PBI) membrane was used as an electrolyte membrane instead of DOPO-di-34DFA of Formula 4 in the preparation of the cathode.

Figure 13:
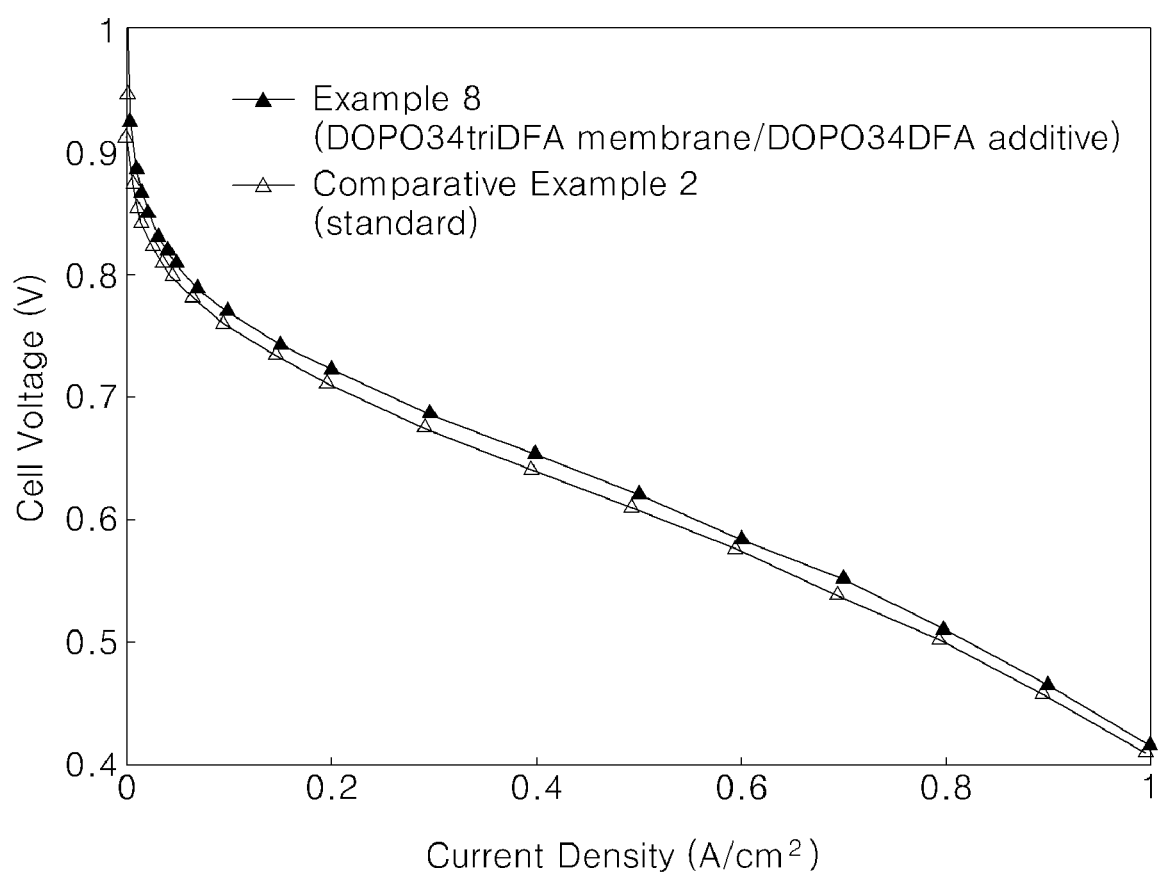
FIG. 13 is a graph showing the changes in cell voltage as a function of the current density of the fuel cells prepared in Example 8 and Comparative Example 2.

The changes in cell voltage as a function of the current density of the fuel cells prepared in Example 8 and Comparative Example 2 were measured, and the results are shown in FIG. 13. Referring to FIG. 13, the performance of the MEA prepared in Example 8 is better when compared with that of the MEA prepared in Comparative Example 2.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those of ordinary skill in the art that changes may be made in these embodiments without departing from the principles and spirit of the invention, the scope of which is defined in the claims and their equivalents.

What is claimed is:

1. An electrolyte membrane for a fuel cell comprising a polymer of a phosphorus containing monomer, wherein:
   the polymer is a polymerization product of the phosphorus containing monomer or a polymerization product of the phosphorus containing monomer and a crosslinkable compound,
   the phosphorus containing monomer is represented by Formula 1, <Formula 1>

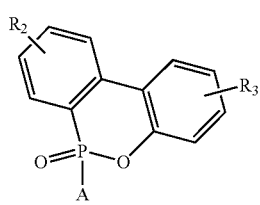

A is a substituted or unsubstituted $C_1$-$C_{20}$ heterocyclic group, a substituted or unsubstituted $C_4$-$C_{20}$ cycloalkyl group, or a substituted or unsubstituted $C_1$-$C_{20}$ alkyl group, and $R_2$ and $R_3$ are each, independently, hydrogen, a $C_1$-$C_{20}$ alkyl group, a $C_1$-$C_{20}$ alkoxy group, a $C_6$-$C_{20}$ aryl group, a $C_6$-$C_{20}$ aryloxy group, a $C_1$-$C_{20}$ heteroaryl group, a $C_1$-$C_{20}$ heteroaryloxy group, a $C_4$-$C_{20}$ cycloalkyl group, a $C_1$-$C_{20}$ heterocyclic group, a halogen, a cyano group, or a hydroxyl group.

2. The electrolyte membrane of claim 1, further comprising at least one proton conductor selected from the group consisting of phosphoric acid and a $C_1$-$C_{20}$ organic phosphonic acid.

3. The electrolyte membrane of claim 1, wherein A is one of the groups represented by the following formulae:

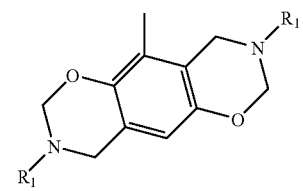

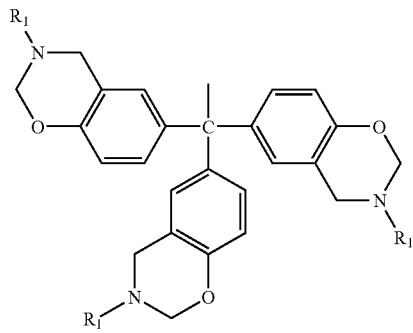

wherein $R_1$ is hydrogen, a $C_1$-$C_{20}$ alkyl group, a $C_1$-$C_{20}$ alkoxy group, a $C_6$-$C_{20}$ aryl group, a $C_6$-$C_{20}$ aryloxy group, a halogenated $C_6$-$C_{20}$ aryl group, a halogenated $C_6$-$C_{20}$ aryloxy group, a $C_1$-$C_{20}$ heteroaryl group, a $C_1$-$C_{20}$ heteroaryloxy group, a halogenated $C_1$-$C_{20}$ heteroaryl group, a halogenated $C_1$-$C_{20}$ heteroaryloxy group, a $C_4$-$C_{20}$ cycloalkyl group, a halogenated $C_4$-$C_{20}$ cycloalkyl group, a $C_1$-$C_{20}$ heterocyclic group, or a halogenated $C_1$-$C_{20}$ heterocyclic group.

4. The electrolyte membrane of claim 1, wherein the phosphorus containing monomer is at least one group selected from the group represented by Formula 2 or 3:

<Formula 2>

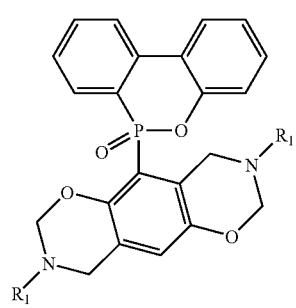

<Formula 3>
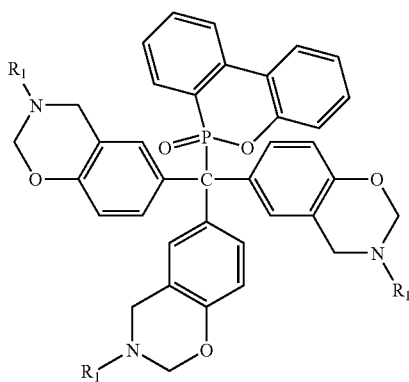
wherein R₁ is one of the groups represented by the following formulae:
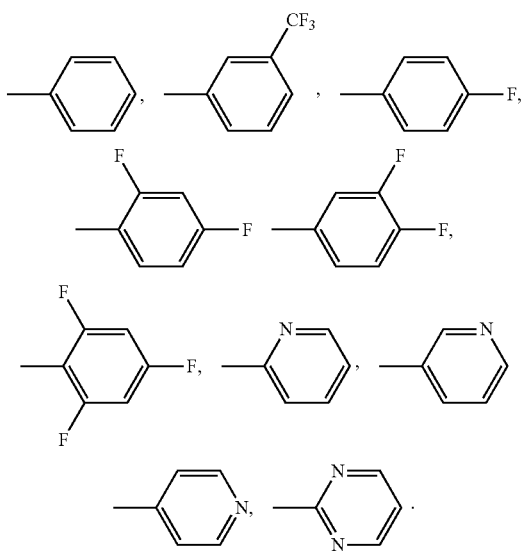
5. The electrolyte membrane of claim 4, wherein the compound represented by Formula 2 or 3 is a compound selected from the group consisting of Formulae 4 through 10 below:
<Formula 4>
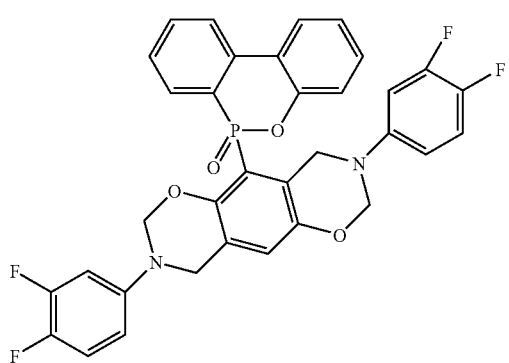
<Formula 5>
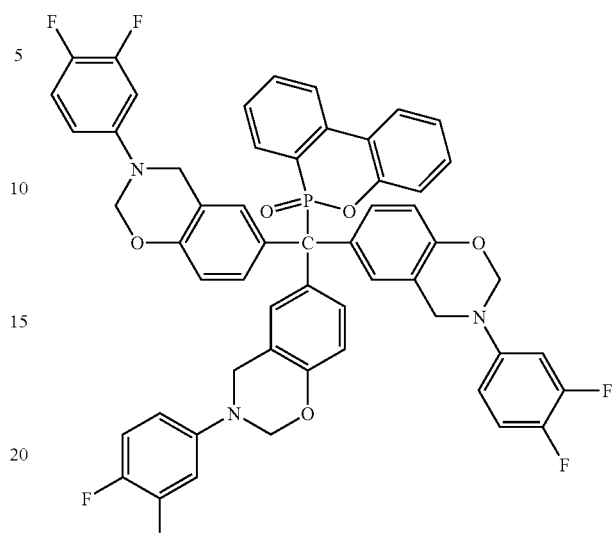
<Formula 6>
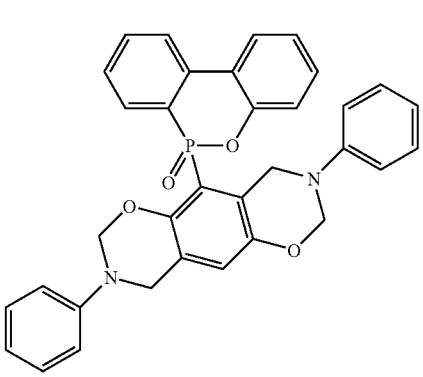
<Formula 7>
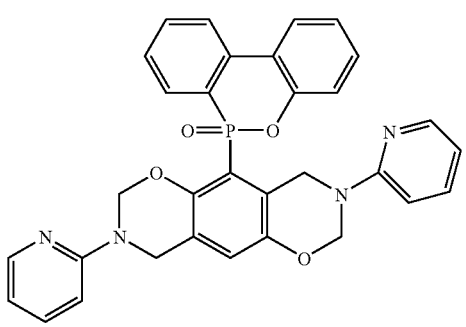
<Formula 8>
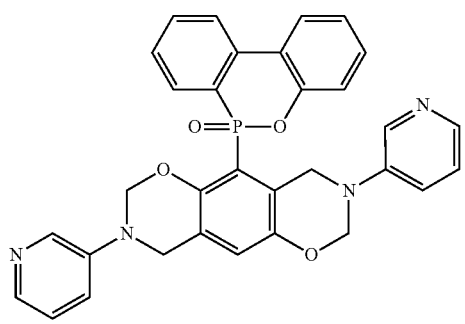

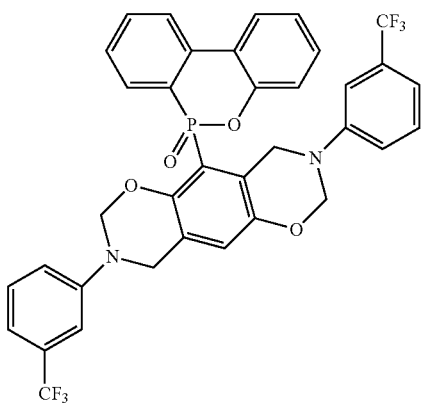
<Formula 9>
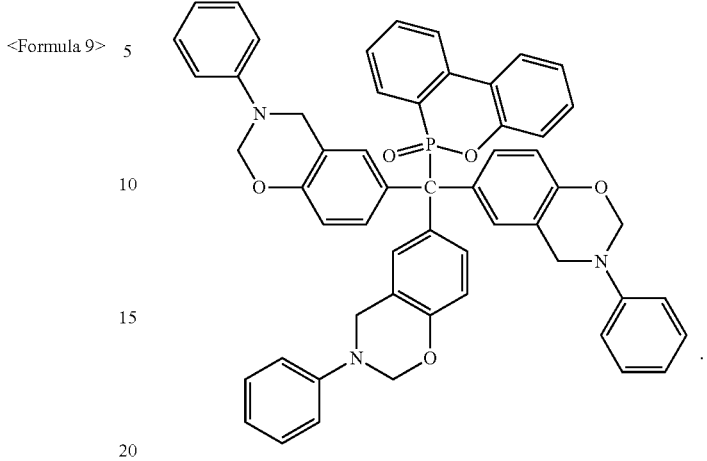
<Formula 10>
* * * * *